(12) United States Patent
Huwais

(10) Patent No.: US 10,912,595 B2
(45) Date of Patent: Feb. 9, 2021

(54) ANCHOR SCREW WITH CONDENSING ATTRIBUTES

(71) Applicant: Huwais IP Holding LLC, Jackson, MI (US)

(72) Inventor: Salah Huwais, Jackson, MI (US)

(73) Assignee: Huwais IP Holding LLC, Jackson, MI (US)

(*) Notice: Subject to any disclaimer, the term of this patent is extended or adjusted under 35 U.S.C. 154(b) by 301 days.

(21) Appl. No.: 16/074,174

(22) PCT Filed: Feb. 6, 2017

(86) PCT No.: PCT/US2017/016635
§ 371 (c)(1),
(2) Date: Jul. 31, 2018

(87) PCT Pub. No.: WO2017/136801
PCT Pub. Date: Aug. 10, 2017

(65) Prior Publication Data
US 2020/0155210 A1 May 21, 2020

Related U.S. Application Data

(60) Provisional application No. 62/292,343, filed on Feb. 7, 2016.

(51) Int. Cl.
*A61B 17/86* (2006.01)
*A61B 17/70* (2006.01)
(Continued)

(52) U.S. Cl.
CPC ........ *A61B 17/863* (2013.01); *A61B 17/7035* (2013.01); *A61B 17/1615* (2013.01);
(Continued)

(58) Field of Classification Search
CPC ......................................... A61B 17/86–17/866
See application file for complete search history.

(56) References Cited

U.S. PATENT DOCUMENTS 2,489,179 A    11/1949  Hartman
3,858,942 A *  1/1975  Humlong ............ B60B 27/023
                                                     301/110.5
(Continued)

FOREIGN PATENT DOCUMENTS

CN    2232727    8/1996
CN    2318985    5/1999
(Continued)

*Primary Examiner* — Zade Coley
(74) *Attorney, Agent, or Firm* — Endurance Law Group PLC

(57) ABSTRACT

An anchor to be screwed into a hole and self-lock therein with high initial stability. The anchor has an aggressively-threaded, self-tapping apical end. A central region of the anchor is formed with a plurality of helical flutes and intervening lands. Each land carries a condensing edge. The condensing edges are configured to apply a circumferentially sweeping compressive strain to the interior surface of the host material while the anchor is being screwed into position. A coronal end of the anchor includes a corking feature to mitigate mushrooming around the perimeter of the hole. A helical groove intersects the condensing edges and flutes. The helical groove has a variable pitch and a decreasing depth which functions to squeeze and displace trapped host material thereby enhancing stability and other benefits. In bone applications, the groove hosts material chips which promote and enhance healing.

12 Claims, 14 Drawing Sheets

(51) Int. Cl.
*A61B 17/16* (2006.01)
*A61C 8/00* (2006.01)

(52) U.S. Cl.
CPC ..... *A61B 2017/8655* (2013.01); *A61C 8/0024* (2013.01); *A61C 8/0025* (2013.01)

(56) References Cited

U.S. PATENT DOCUMENTS

| | | | |
|---|---|---|---|
| 5,489,179 A | | 2/1996 | Gabriel et al. |
| 5,536,127 A | | 7/1996 | Pennig |
| 5,702,443 A | * | 12/1997 | Brånemark ........ A61B 17/8625 606/314 |
| 5,816,812 A | | 10/1998 | Kownacki et al. |
| 5,891,146 A | | 4/1999 | Simon et al. |
| 6,048,204 A | | 4/2000 | Klardie et al. |
| 6,149,432 A | | 11/2000 | Shaw et al. |
| 6,264,677 B1 | | 7/2001 | Simon et al. |
| 6,386,877 B1 | * | 5/2002 | Sutter ................ A61C 8/0018 433/173 |
| 6,402,515 B1 | | 6/2002 | Palti et al. |
| 6,641,395 B2 | | 11/2003 | Kumar et al. |
| 6,679,701 B1 | * | 1/2004 | Blacklock ........... A61C 8/0022 433/174 |
| 7,008,227 B2 | | 3/2006 | Carmichael et al. |
| 7,300,281 B2 | | 11/2007 | Cantatore et al. |
| 8,277,218 B2 | | 10/2012 | D'Alise |
| 9,326,778 B2 | | 5/2016 | Huwais |
| 9,737,312 B2 | | 8/2017 | Huwais |
| 9,918,764 B2 | | 3/2018 | Huwais |
| 2003/0165795 A1 | | 9/2003 | Stucki-McCormick |
| 2004/0223830 A1 | | 11/2004 | Panasik et al. |
| 2004/0230195 A1 | | 11/2004 | Kaikkonen et al. |
| 2005/0118550 A1 | | 6/2005 | Turri |
| 2005/0273110 A1 | | 12/2005 | Boehm et al. |
| 2006/0018733 A1 | * | 1/2006 | Dill ..................... F16B 15/06 411/499 |
| 2006/0111724 A1 | | 5/2006 | Ping |
| 2007/0037117 A1 | | 2/2007 | Jaunberzins |
| 2007/0099153 A1 | | 5/2007 | Fromovich |
| 2009/0136898 A1 | | 5/2009 | Kim |
| 2009/0142731 A1 | | 6/2009 | Kim |
| 2009/0259227 A1 | | 10/2009 | Ahn |
| 2010/0055645 A1 | | 3/2010 | Mullaly et al. |
| 2010/0330534 A1 | | 12/2010 | Hyun |
| 2011/0070558 A1 | | 3/2011 | Park et al. |
| 2012/0197311 A1 | | 8/2012 | Kirschman |
| 2012/0244497 A1 | | 9/2012 | Huwais |
| 2015/0044638 A1 | | 2/2015 | Baez |
| 2015/0157425 A1 | | 6/2015 | Shalom |
| 2015/0297275 A1 | * | 10/2015 | Huwais .................. A61C 8/005 606/315 |
| 2017/0071702 A1 | | 3/2017 | Fromovich |
| 2017/0348073 A1 | | 12/2017 | Mamraev et al. |

FOREIGN PATENT DOCUMENTS

| | | | |
|---|---|---|---|
| CN | 1246040 A | 3/2000 | |
| CN | 2724645 | 9/2005 | |
| CN | 101229072 A | 7/2008 | |
| CN | 101292906 A | 10/2008 | |
| CN | 105120792 A | 12/2015 | |
| EP | 0530160 A1 | 3/1993 | |
| EP | 1273273 A2 | 1/2003 | |
| EP | 1749498 A1 | 2/2007 | |
| EP | 1752109 B1 | 10/2010 | |
| EP | 2931169 B1 | 7/2018 | |
| IL | 210929 | 4/2011 | |
| KR | 101128730 B1 | 3/2012 | |
| WO | 2001037758 A3 | 5/2002 | |
| WO | 2007086622 A1 | 8/2007 | |
| WO | 2011053588 A1 | 5/2011 | |
| WO | WO-2014093487 A1 * | 6/2014 | ............ A61C 8/006 |
| WO | 2014149746 A1 | 9/2014 | |
| WO | 2015168332 A2 | 11/2015 | |
| WO | 2015172842 A1 | 11/2015 | |
| WO | 2015168332 A3 | 12/2015 | |

* cited by examiner

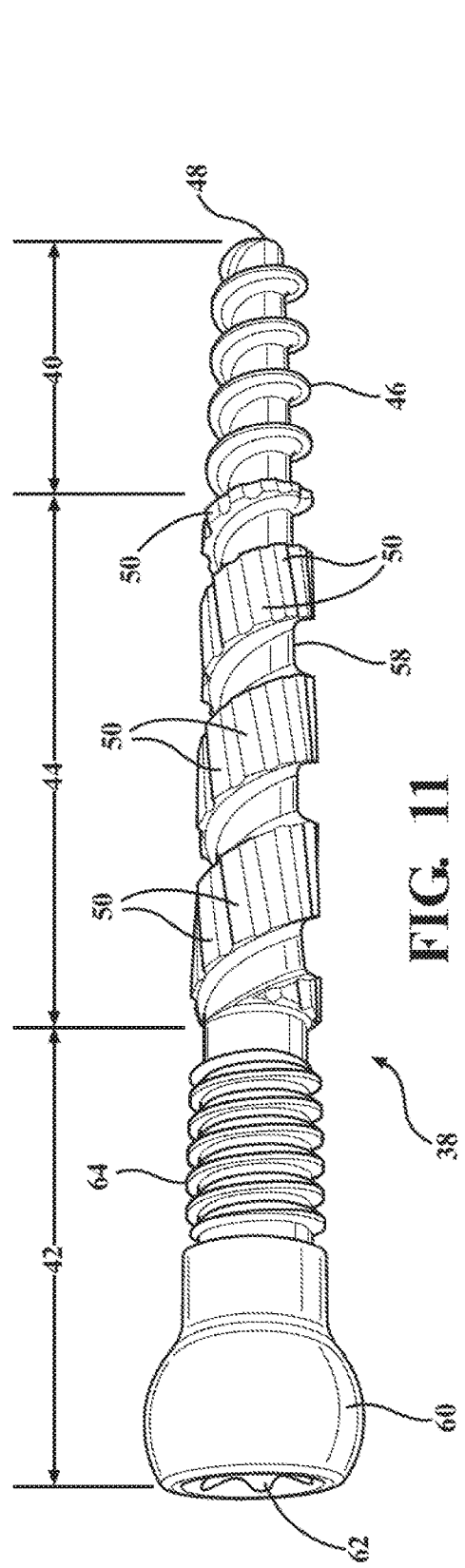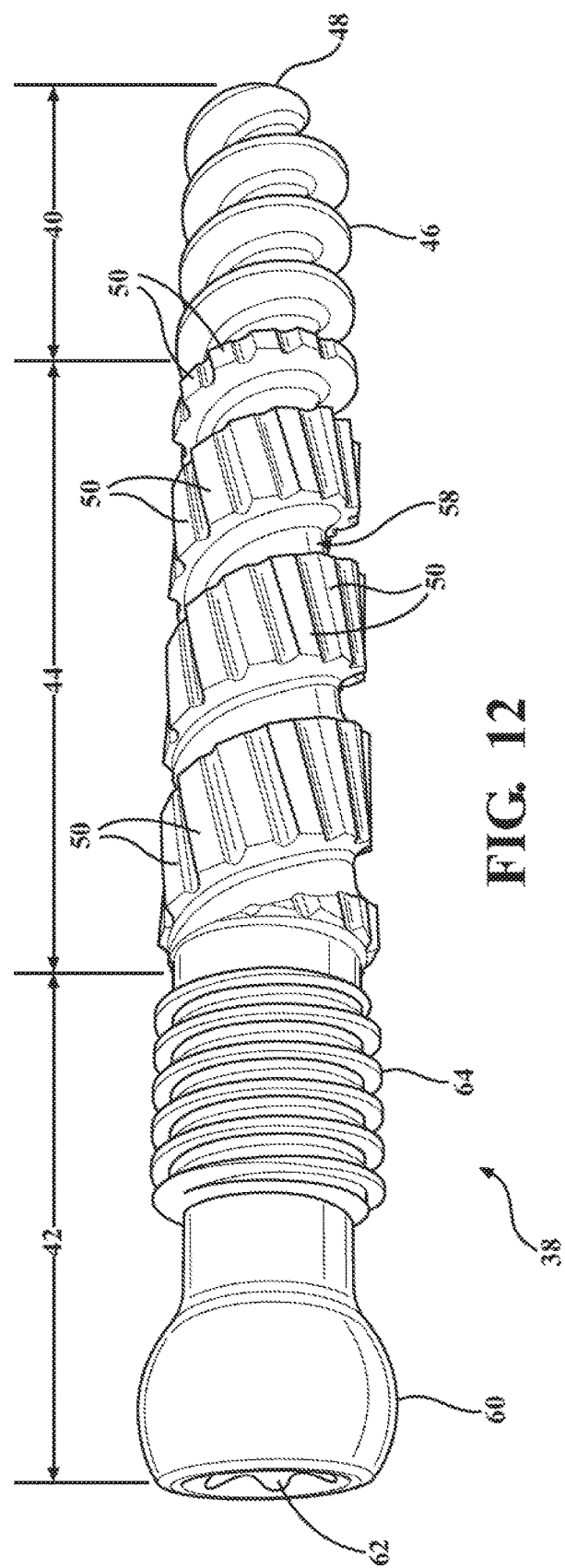

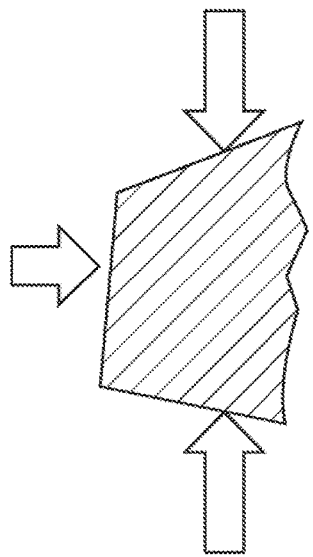
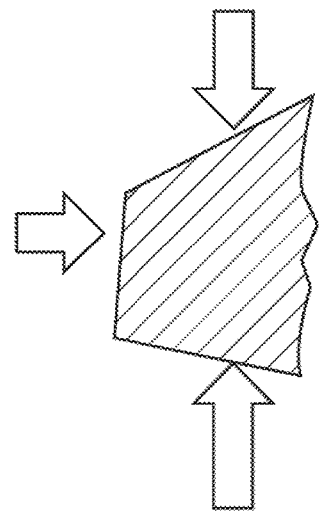
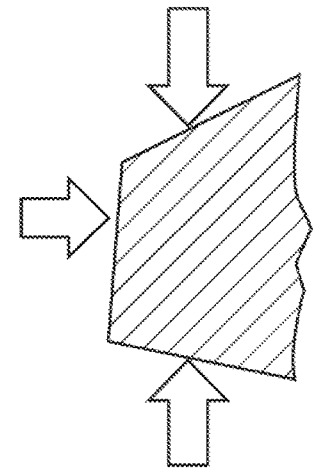
FIG. 16A    FIG. 16B    FIG. 16C
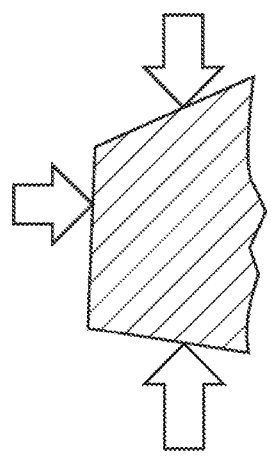
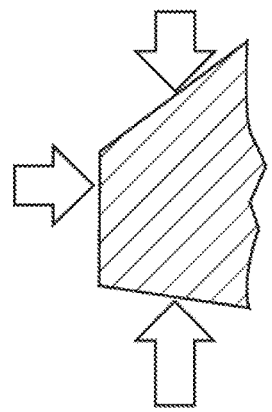
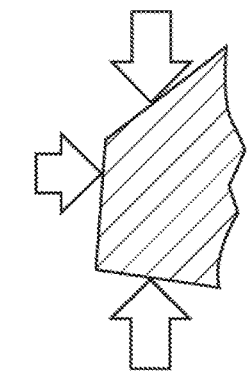
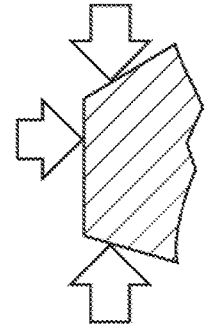
FIG. 16D    FIG. 16E    FIG. 16F    FIG. 16G

ANCHOR SCREW WITH CONDENSING ATTRIBUTES

BACKGROUND OF THE INVENTION

Field of the Invention

The invention relates generally to anchors intended to provide fixation in a host material, and more particularly to anchors designed to produce compaction in the host material as the anchor is screwed into position, and even more particularly to such anchors placed in living organic materials like bone.

Description of Related Art

Screw-in anchors are used in many applications. For example, in industrial and construction settings, where the host material is wood or concrete or metal or polymer, an anchor may be placed in a wall or other member to provide a fixed point of connection to attach another element. Screw-in anchors are used extensively in medical applications, where the host material is bone, to provide a fixed point of connection for metal plates, pins, rods, Kirschner wires and intramedullary devices such as the Kuntscher nail and interlocking nail, among many other uses.

Dental anchors are another form of screw-in anchor where the host material is bone. A dental anchor, also known as an endosteal implant or fixture, is a surgical device used to support a crown, bridge of teeth, denture, facial prosthetic or to act as an orthodontic anchor. Typically, such anchors are designed as threaded, tapered implants that are not loaded immediately after setting in order that full stability may be reached over time as the surrounding bone grows into the crevices of and around the anchor. Several months may be required for bone ingrown until the anchor reaches sufficient stability to be put into normal service.

In many applications, anchor stability is a key consideration because the anchor must be able to support the intended loading. When the host material is not organic, living tissue, maximum anchor stability is usually achieved immediately after placement. For these situations, the anchor should be designed to maximize initial stability. In applications where the host material is an organic living material, like bone or wood for example, reaching full anchor stability may require the passage of time for healing and in-growth after placement. In these latter cases, the faster an anchor can reach sufficient stability, the better.

Anchors that possess sufficient stability at the time of initial placement are highly valued. Although the prior art is composed of a great many different designs and concepts aimed at improving anchor stability—both initial and long-term—there remains a continuing desire for improvement. Specifically, anchor stability remains a long-felt need in the art where improvements are readily embraced.

BRIEF SUMMARY OF THE INVENTION

According to one aspect, this invention relates to an anchor of the type that is screwed into a host material. The host material may be of any suitable type. The anchor comprises a body having an apical end and a coronal end and a central region. The central region is disposed between the apical end and the coronal end. The apical end has an apical thread profile, the purpose of which is to advance the body progressively deeper into the hole as the body is forcibly turned in a first rotary direction. The central region includes an array of longitudinally extending flutes with intervening lands. Each flute has a depth. Each land forms a condensing edge that is configured to apply a circumferentially sweeping compressive strain to the interior surface of the host material with a densifying action while the anchor is being screwed into position. And at least one helical groove spirals along the central region and intersects each condensing edge at least once According to another aspect of this invention, a pedicle screw comprises a body having an apical end and a coronal end. A central region of the body extends between the apical end and the coronal end. The apical end has an apical thread profile for advancing the body progressively deeper into an osteotomy as the body is forcibly turned in a first rotary direction. The central region includes an array of longitudinally extending flutes with intervening lands. Each flute has a depth. Each land forms a condensing edge configured to apply a circumferentially sweeping compressive strain to the interior surface of the osteotomy with a densifying action while the pedicle screw is being screwed into the osteotomy. At least one helical groove spirals along the central region and intersects each condensing edge at least once.

The invention also contemplates a method for screwing an anchoring into position, in which host material trapped between the apical thread profile and inside the helical groove is progressively squeezed and manipulated as the anchor is screwed into place. This squeezing and displacement densifies the host material in contact to the anchor, resulting in increased primary stability between the host material and the anchor. In instances where the host material is a living organic, like bone or wood, this progressive squeezing and displacement promotes rapid new growth formations.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 11 is a perspective view of the smaller size anchor of FIG. 9 with call-outs identifying different sections thereof;

FIG. 12 is a perspective view of the larger size anchor of FIG. 7 with call-outs identifying the different sections;

FIGS. 16A-16G are cross-sections of the host material taken inside the apical thread profile and helical groove at respective locations 16A, 16B, 16C, 16D, 16E, 16F and 16G in FIG. 16, with arrows indicating pressure.

DETAILED DESCRIPTION OF THE INVENTION

The present invention is directed toward an anchor of the type screwed into a host material for a variety of applications. The anchor is well-suited to installations into which an optimally-sized hole is first prepared in the host material, however self-tapping applications are also possible. Furthermore, the anchor is perhaps best-suited to applications where the host material has some elastic properties, and even more ideally to host materials having viscoelasticity properties which exhibit a degree of time-dependent strain. Host materials include, but are not limited to, bone, wood, cellular compositions, foam metals, amorphous polymers, semi-crystalline polymers, biopolymers, and the like. One presently preferred host material is in vivo bone, wherein the anchor is used to provide a solid foundation for an implant or other surgical device. It must be understood, that although the following descriptions make frequent reference to certain surgical/orthopedic applications, the anchor may be used to great effect in various industrial and other non-surgical settings.

Figure 2:
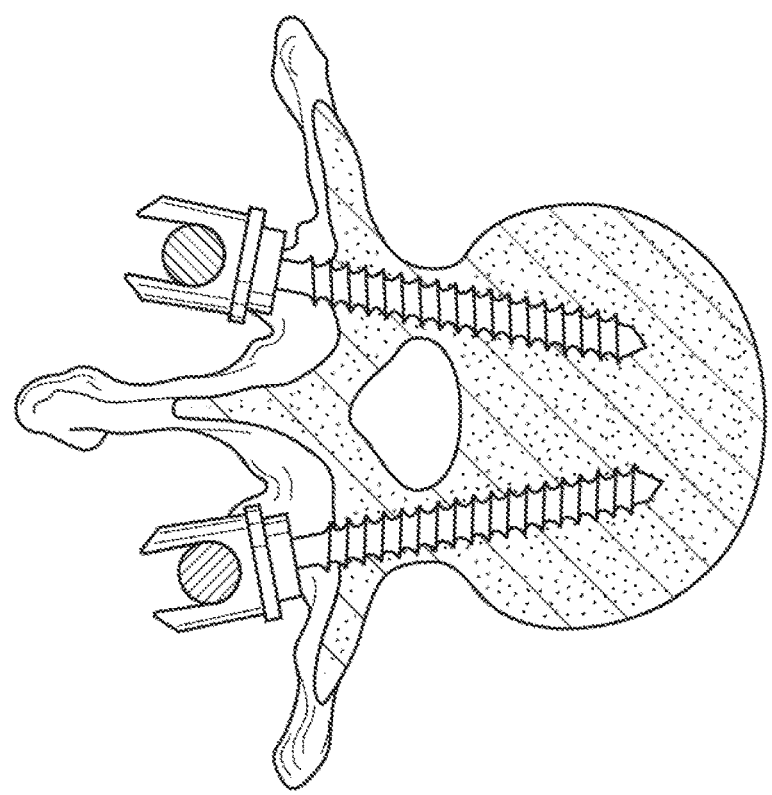
FIG. 2 is a cross-sectional view taken generally along lines 2-2 of FIG. 1 showing how the pedicle screws are typically placed into the vertebral body through the pedicles of a vertebrae.
Figure 1:
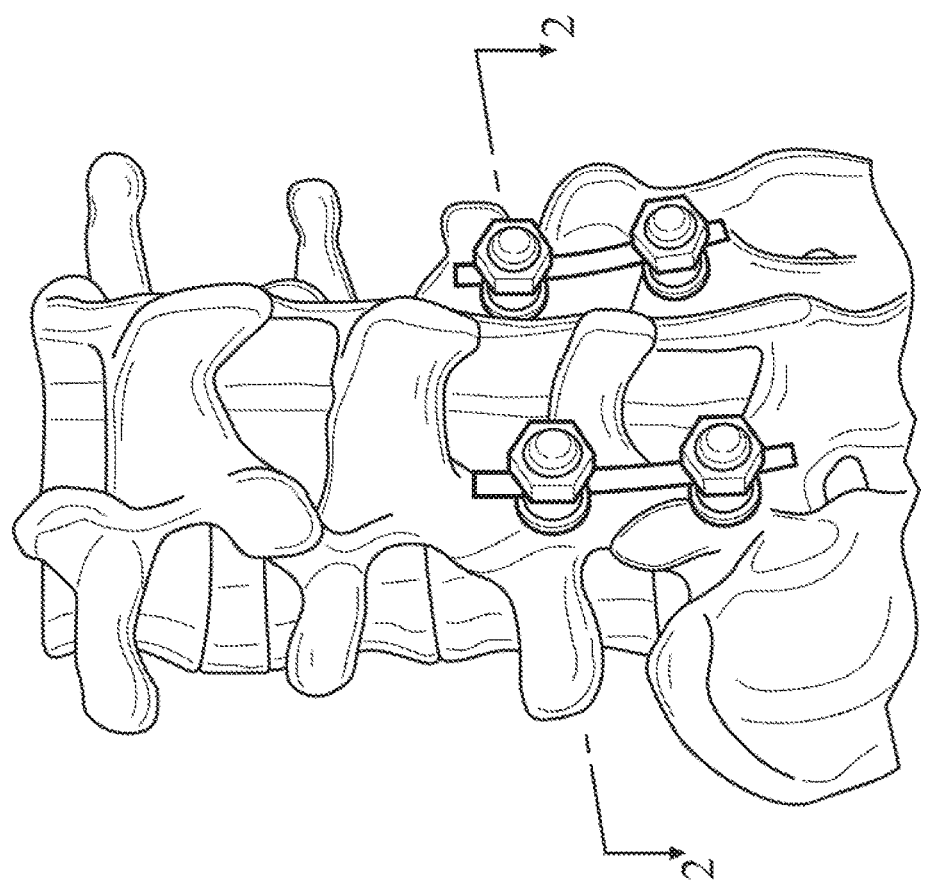
FIG. 1 is a fragmentary perspective view showing a lumbar surgical procedure, in which anchors are employed in the form of pedicle screws.

FIGS. 1 and 2 show an exemplary orthopedic application in the form of spinal stabilization. Spinal stabilization, also known as spinal fusion, is an invasive type of surgery often performed to address issues of low back pain. Spinal fusion permanently connects two or more vertebrae in the spine, eliminating relative motion between them. In many cases, surgeons will use plates, anchors (known in this context as a pedicle screw) and rods to help hold the spine still so the vertebrae can heal into one solid unit. These illustrations demonstrate common prior art examples, with two pedicles screws shown in the cross-sectional FIG. 2 penetrating down the isthmus of the pedicles into the vertebral body. Extreme care is taken to avoid penetration of the spinal canal as well as the vertebral body cortex at the depth of insertion. Ideally, the two pedicle screws should stay entirely within the cortex of the pedicles and the vertebral body.

Pedicle fixation systems like these have emerged as a popular technique, however instances of fusion failure are unacceptably high. One well-documented failure mode is attributed to the instability of the pedicle screws. Because significant forces are applied to the spine through the pedicle screw fixation points in relatively soft bone, over time there is an elevated risk of failure at the bone-metal junction.

Pedicle screws as well as other forms of threaded anchors are often inserted into previously prepared holes. This is particularly true when the host material is bone, but likewise common for many other types of host materials. A hole formed in bone is sometimes referred to as an osteotomy. Regardless of the host material composition, the technique used to form the hole can have a significant impact on the physical properties or attributes of the side walls that establish the interior periphery of the hole. That is to say, the way the hole is formed can affect the stability of the anchor-to-host juncture. For example, a standard drilling technique using a twist drill is known to cut and excavate the host material to form the hole. In these cases, the interior side walls of the hole will retain a very similar composition to the overall surrounding host material in terms of density, residual strain and such. An altogether different example of hole formation is described with reference to FIGS. 3-6. This latter technique, known variously as rotary densifying, rotary condensing and osseodensification (in bone applications), is characterized by expansion of a pilot hole while auto-grafting the small amounts of created particulate back into the side walls so that little-to-no host material is removed. A detailed description of this technique may be found in WO 2015/138842, published Sep. 17, 2016, and WO 2014/077920, published May 22, 2014, both assigned to the Applicant of this present invention. The entire disclosures of these references are hereby incorporated by reference as permitted by applicable laws in each jurisdiction.

Figure 17:
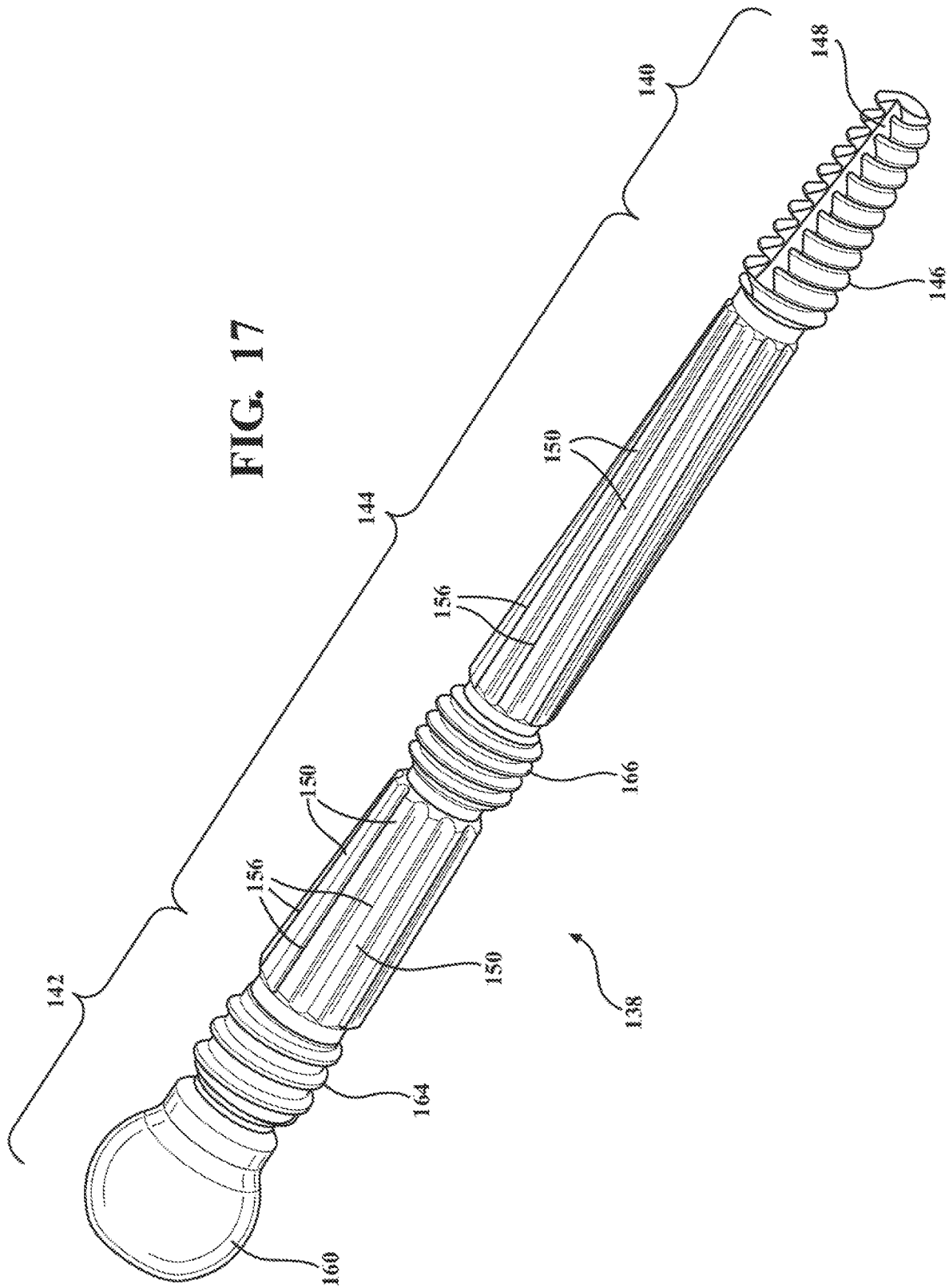
FIG. 17 is a perspective view of alternative anchor embodiment.

In the example of FIGS. 3-6, a hole 20 is formed in a host material 22 in preparation to receive a screw-in anchor like that shown in FIG. 11, 12 or 17. These examples contemplate an application where the host material 22 is bone, in which case the hole 20 may be referred to as an osteotomy. In such cases, the intended anchor to be installed into the fully prepared hole 20 will have a known screw length and a known diameter specially selected to meet the requirements of the application. The dimensions of the anchor are an important factor in preparing the hole 20. In the case of a pedicle screw, for example, the implanted length of the anchor may be on the order of about 42 mm and the diameter may be in the range of about 4.5 mm to about 6.5 mm. In the case of a dental implant, for another example, the implanted diameter of the anchor may be on the order of about 3-9 mm and the length may be in the range of about 5-20 mm. Of course, these are exemplary measurements; the specific application will dictate the desired anchor dimensions. Typically, the depth of the fully-formed hole 20 will be approximately equal to the length of the anchor to be later inserted into the hole 20.

Figure 3:
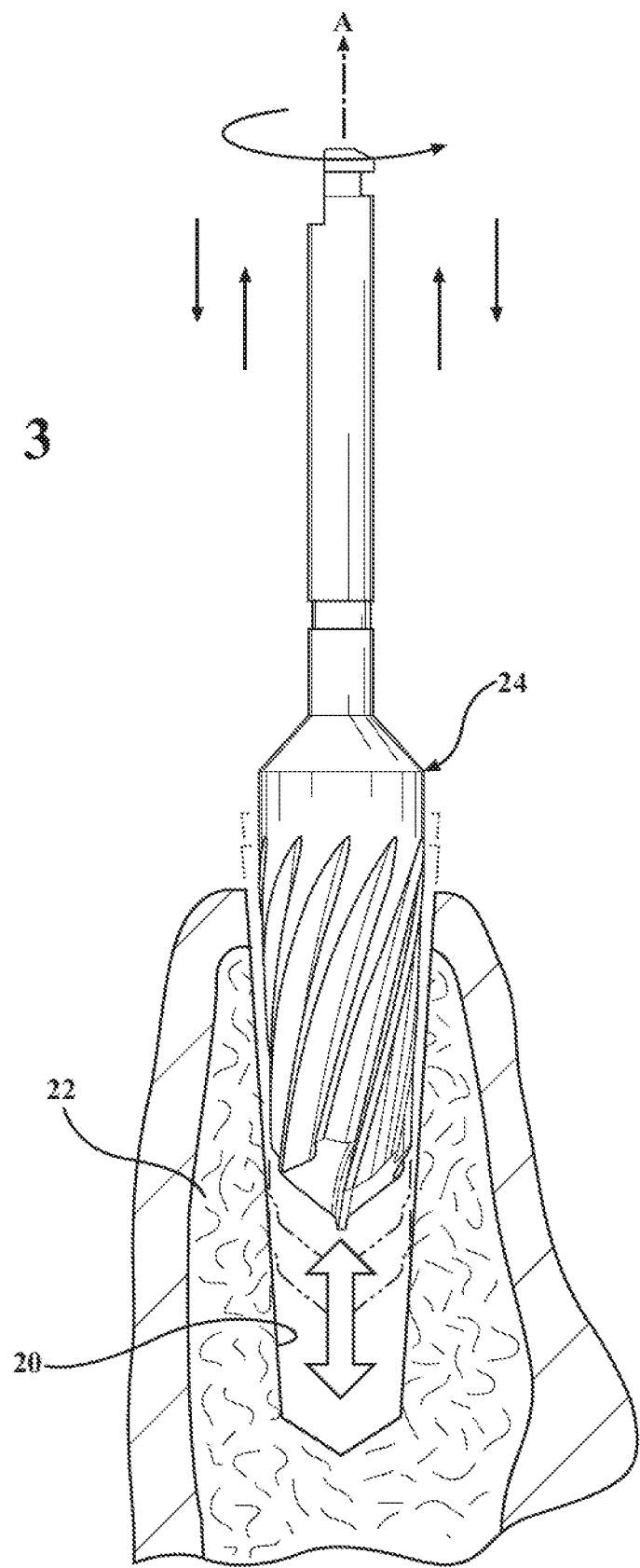
FIG. 3 is a simplified cross-sectional view showing a preparatory hole-forming procedure using a tool referred to herein as a bur and in which, in one of the contemplated applications, can be performed in a host material composed of in vivo bone.

Continuing with the surgical context as an example, the osseodensification method of hole formation begins with drilling a pilot hole to a specified depth. The specified depth may be equal to, slightly more, or slightly less than the implanted length of the anchor. The diameter of the pilot hole may, for example, be on the order of 1.5 mm for an anchor diameter in the range of about 3-7 mm. A specially designed bur 24 is coupled to a high-speed drill motor (not shown). The bur 24 has a tapered body formed with helical flutes and blades. Each blade has a working edge that rubs across the inside walls of the hole without cutting when the bur 24 is rotated at high speed in a non-cutting direction. The friction and heat created by the rubbing action are controlled on-the-fly by altering the pressure and/or irrigation flow. Because the body of the bur 24 is tapered, the surgeon/operator may at any time lift the working edges away from contact with the inside surfaces of the hole to allow cooling. This can be done in a controlled "bouncing" fashion, as indicated in FIG. 3, where pressure is applied in short bursts with the surgeon/operator continuously monitoring progress and making fine corrections and adjustments. As the downward applied force increases, eventually the stresses in the host material 22 exceed its yield strength. When this happens, the working edges will plow through the surface thus progressively enlarging the diameter of the hole 20 until the bur 24 reaches full/maximum depth. The bur 24 is removed and a different larger bur 24 is used to repeat the process and thereby achieve expansion of the hole 20. This process is repeated as needed until the diameter of the hole 20 is sized to receive the intended anchor.

Figure 4:
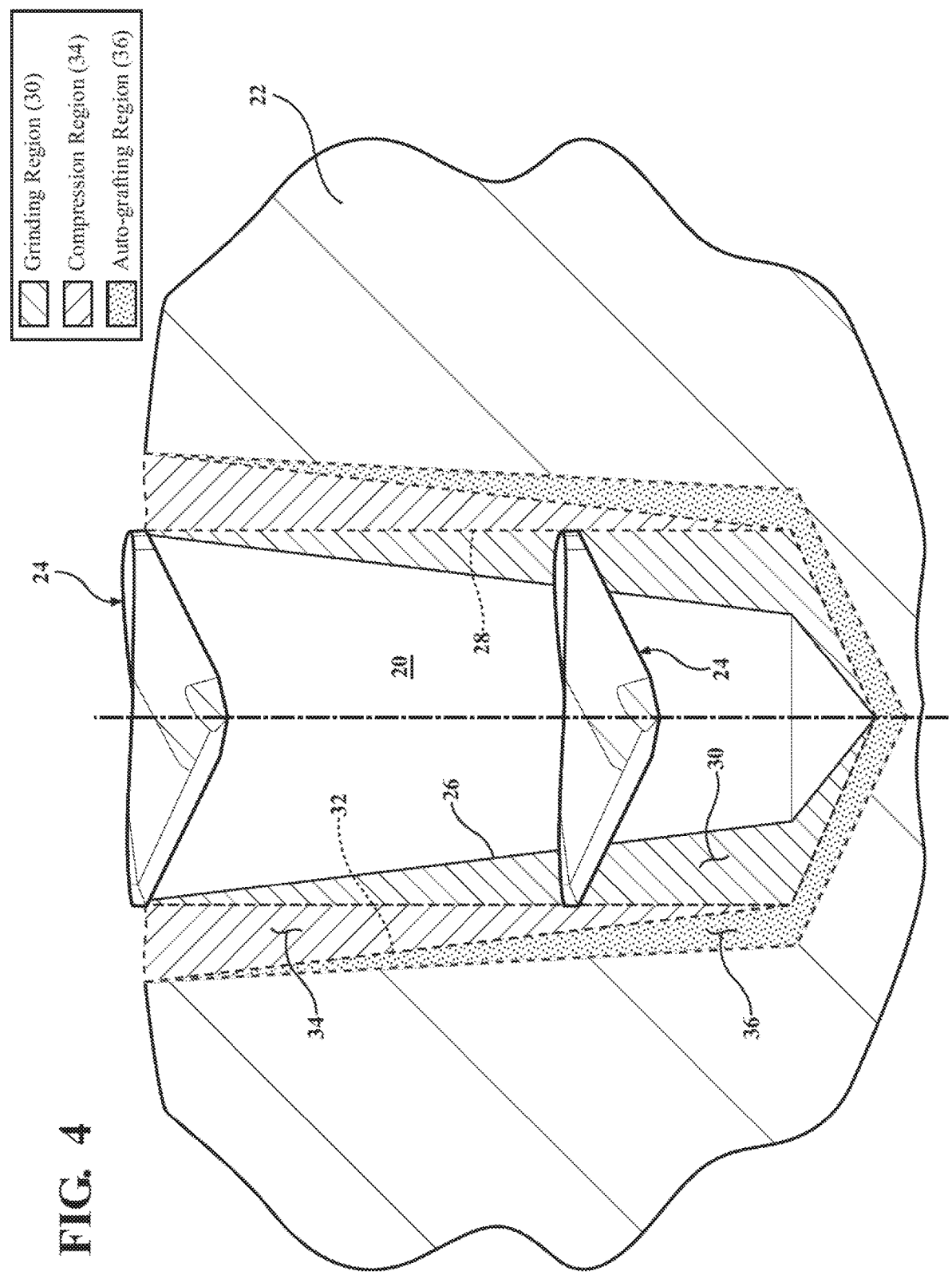
FIG. 4 is an exaggerated cross-section through a hole using a progressively larger series of burs as in FIG. 3, with the apical end of a bur shown at various stages of the expansion procedure in order to describe the zones of the surrounding host material that experience grinding, compaction and auto-grafting with each stage of the hole-forming process.
Figure 5:
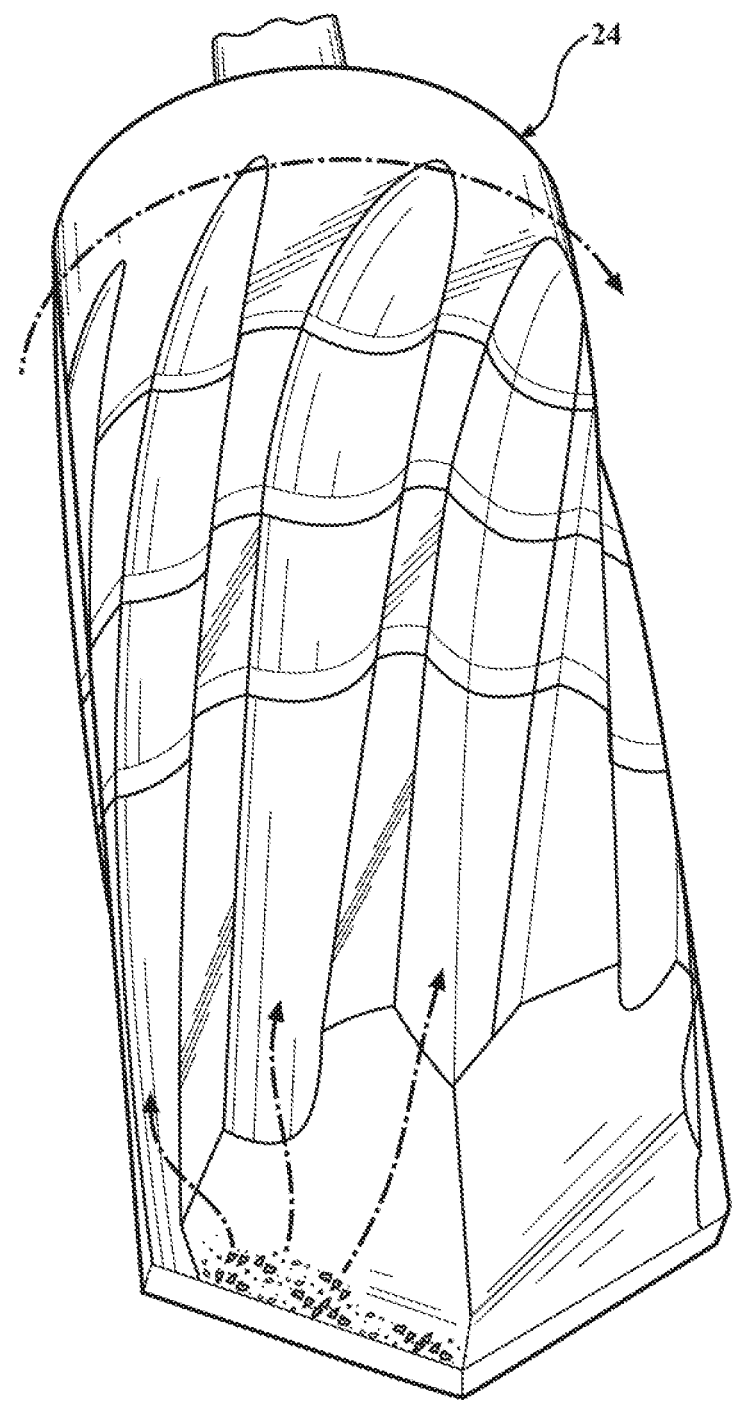
FIG. 5 is a perspective view of the apical end of the bur as in FIG. 3 illustrating the region of the apical end where particles of the host material are routed for repatriation into surrounding walls of the hole.

FIG. 4 illustrates the ability of the bur 24 to simultaneously auto-graft and compact particles of the host material 22. The compaction aspect may be defined as the gentle push of the host material structure laterally outwardly to compact the constituent molecules throughout the region surrounding the hole 20. In FIG. 4, a hole 20 formed by the rotary compaction method is shown with exaggerated taper on the order of ~7° (as compared with a more typical taper angle in the range of about 2°-3°) to highlight the necessary grinding of a small amount of host particles with each progressively larger bur 24.

In FIG. 4, surface 26 indicates the inner wall of the hole 20 as would have been prepared in a preceding expansion operation by a different bur of slightly smaller size (not shown). The leading end of the next incrementally larger size bur 24 is shown in solid about to enter the osteotomy and shown again approximately ⅔ into the hole 20. Construction line 28 indicates the cylindrical path of the bur's leading end as it moves from top to bottom within the hole 20. The diameter of the path 28 of the leading end naturally remains constant over the distance it travels. When the bur 24 first enters the hole 20 as shown in solid, the internal diameter of the prior hole 26 is approximately equal to the diameter of the path 28 of the leading end. However, the internal diameter of the prior hole 26 progressively narrows (i.e., tapers inwardly) toward the bottom of the hole 20 due to the tapered shape of the prior bur of a smaller size (not shown). As the current bur 24 is advanced deeper toward the bottom of the hole 20, more and more host material 22 is ground away and/or displaced to make room for its advancing leading end. Grinding region 30, defined as the space between surfaces 26 and 28, represents the host material 22 that is milled and/or displaced by the outermost edges of the leading end as it makes its way to the full depth of the hole 20. The milled or ground region 30 includes not only the side walls, but also the leading end of the bur 24.

Remaining within the context of FIG. 4, surface 32 indicates the outer wall of the hole 20 as prepared by the expansion operation of bur 24 when its leading end reaches the bottom. The surface 32 is a substantially perfect negative of the revolving body of the bur 24. In other words, the surface 32 will have a taper equal to that of the body of the bur 24, and a bottom impression made by the spinning end of the bur. Compression region 34, defined as the space between surfaces 28 and 32, represents the host material 22 that is plastically displaced as the body of the bur 24 makes its way to the full depth of the hole 20. All of the host material 22 within region 34 is compacted radially outwardly into the surrounding structure without cutting, and therefore represents a zone of densified material.

Wherever the outermost edges of the leading tip contact the host material (i.e., grinding region 30), attrition causes the host material 22 to be ground into particles. Some of the host particles are distributed up the flutes (see FIG. 5) where they are wiped and compacted into the walls of the hole 20. The remainder of the host particles are carried to the bottom of the hole 20 and there wiped and pressed into the bottom. As a result, an auto-grafting region 36 is developed around the compaction region 34, as shown in FIG. 4.

Figure 6:
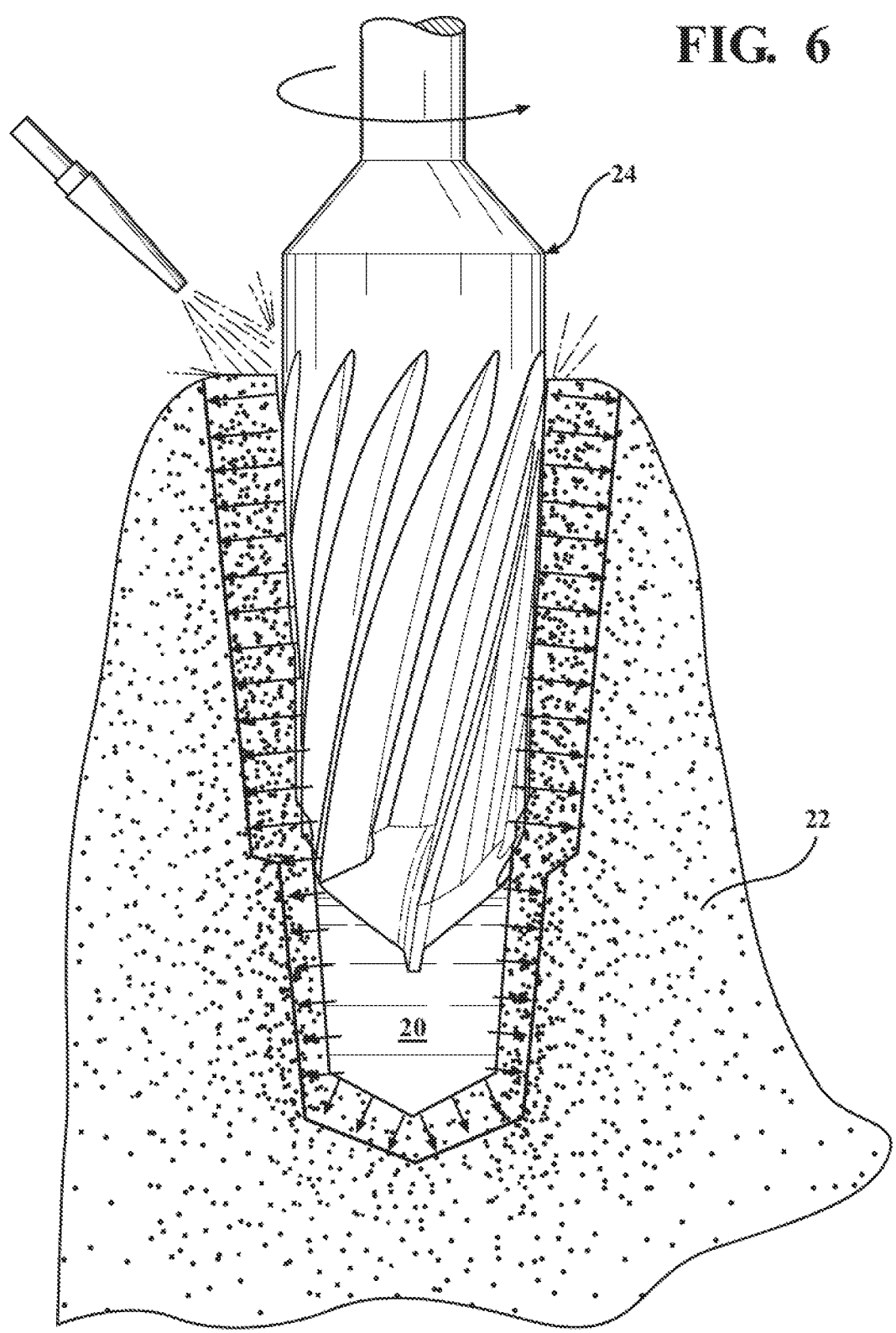
FIG. 6 is a view as in FIG. 3 but showing the bur pressed down into contact with the inner sidewall of the hole in combination with copious external irrigation resulting changes in pressure applied to the inner sidewall of the hole due to hydro-dynamic effects.

FIG. 6 depicts, graphically, the pressure gradients that are exerted against the inner side walls of the hole 20 when the rotary compaction method is combined with a continuous flow of irrigation fluid. The reverse twist of the bur's flutes propels (pumps) the irrigation fluid toward the bottom of the hole 20. Excess irrigation fluid is continually pushed out of the hole 20 in the gap around the bur 24. A hydraulic pressure is created inside the hole 20 according to the general principles of hydraulics and fluid dynamics. The pressure gradient pushes against the side walls, preparing and preconditioning the interior surface of the hole 20. This pressure gradient will increase and decrease in direct response to the amount of force applied by the operator as he or she repeatedly advances and relaxes the rotating bur 24 into the hole 20. By modulating the position of the bur 24 in combination with a continuous supply of irrigation fluid, the operator can apply an evenly distributed, expansive pressure with piston-like effect to the interior of the hole 20—only intermittently touching the walls of the hole 20 with the working edges of the bur 24. This throbbing hydraulic effect has many preconditioning advantages, which include: 1) gentle pre-stressing of the host structure of the hole 20, 2) haptic feedback transmitted through the bur 24 that allows the operator to tactically discern the instantaneously applied pressure prior to actual contact between the bur 24 and side walls, 3) enhanced hydration of the host structure which increases host toughness and increases host plasticity, 4) hydraulically assisted infusion of host fragments into surrounding host material 22, 5) reduced heat transfer, 6) hydrodynamic lubricity, 7) dampening or cushioning of the trauma sensed by or through the host material (e.g., by a patient in the case of surgical applications), and so forth.

When the working edges of the bur 24 breach the hydrodynamic layer, they will perform the compacting action described. In the region of direct contact, the pressure gradient will experience a sharp increase as a result of mechanically applied pressure through the working edges, which in turn causes the host structure to plastically deform. Meanwhile, the irrigating fluid trapped below the bur 24 will continue to apply a preconditioning hydro-static pressure. By axially stroking the rotating body of the bur 24 within the hole 20, the hydraulic pressure inside can be powerfully modulated.

Once the hole 20 has been prepared, a suitable anchor can be screwed therein. In FIGS. 7-16, an anchor according to one exemplary embodiment of this invention is generally shown at 38. The anchor 38 is preferably inserted into a hole 20 prepared using the compaction method described above. Yet, the anchor 38 is not limited to use in holes 20 formed in this manner. Indeed, a suitable hole 20 for the anchor 38 may be formed using traditional drilling/excavating techniques. And in some applications, a prepared hole may not even be required, especially if the anchor 38 is fitted with self-tapping lead threads like those depicted in the alternative example of FIG. 17.

The illustrated anchor 38 is particularly adapted for use as a pedicle screw, however other uses/applications are certainly possible with some alteration to the proportions, including non-spinal orthopedic and dental as well as a wide-variety of industrial uses. Two different size anchors 38 are shown, for comparison purposes, in FIGS. 7-12. A larger size anchor 38 appears in FIGS. 7-8 and 12. A smaller size anchor 38 appears in FIGS. 9-11. Both large and small anchors 38 are shown having the same length, which may be about 45 mm overall. The larger size anchor 38 may be sized to have a diameter of about 6.5 mm, whereas the smaller size anchor 38 may be sized to have a diameter of about 4.5 mm. Of course, these dimensions are configured for the average pedicle screw application. Other applications will very likely require alteration to the dimensional proportions.

Figure 13:
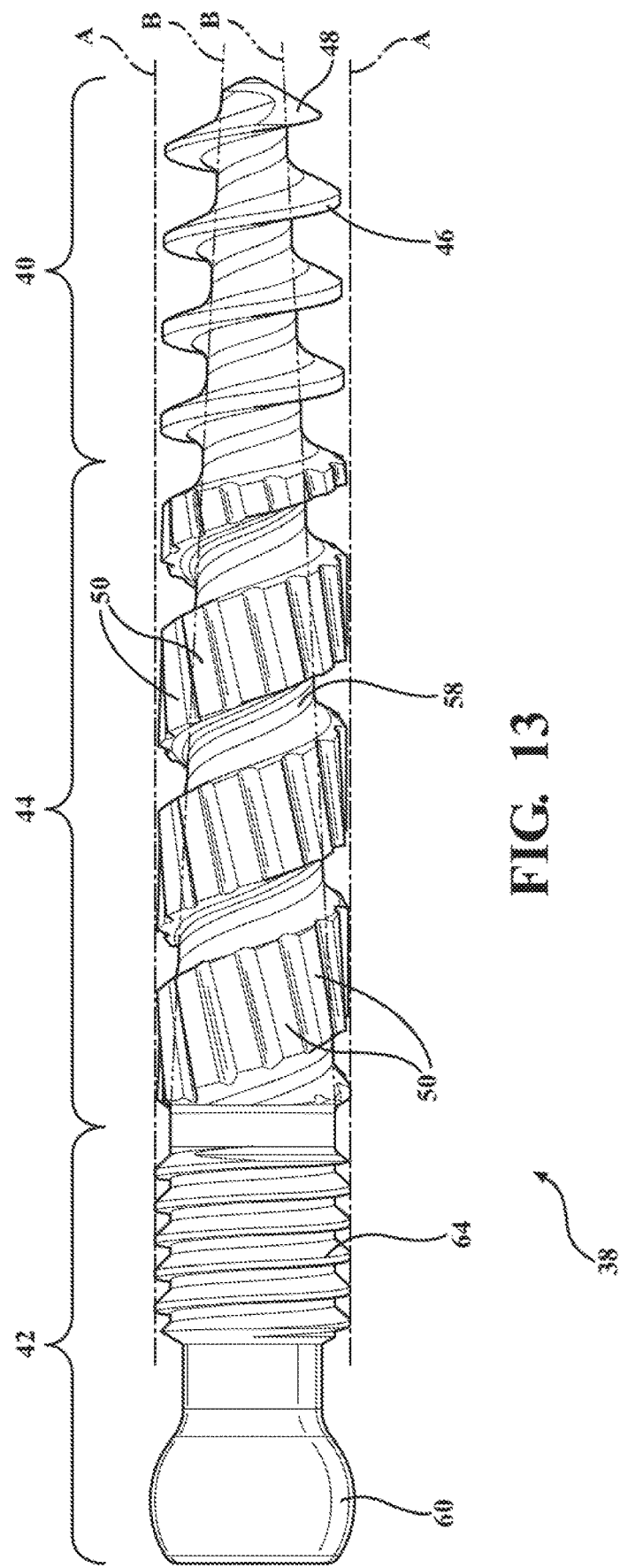
FIG. 13 is a side elevation of an anchor as in FIG. 7 with constructions lines added to describe certain common attributes.

The anchor 38 is shown in FIGS. 11-13 comprising a body formed with a gently tapered outer profile. Parallel construction lines A in FIG. 13 reveal that the taper may be very slight, one the order of 1° or less. The body has at least three discernable sections: an apical end 40 and a coronal end 42 and a central region 44. The apical end 40 forms the leading end of the anchor 38 and in use is inserted first into the prepared hole 20. The central region 44 of the body extends between the apical end 40 and the coronal end 42. In practice, the relative longitudinal lengths of the apical end 40, coronal end 42 and central region 44 can vary relative to the entire longitudinal length of the body. In the illustrated examples, the apical end 40 extends approximately ¼ the overall length of the body, the central region 44 extends about ½ the length of the body, and the coronal end 42 extends approximately ¼ the overall length of the body.

The apical end 40 is formed with an apical thread profile 46 which is shown in one example as an aggressive, V-shaped one-start design. The apical thread profile 46 has a right-hand twist for advancing the anchor 38 progressively deeper into the hole 20 as the body is forcibly turned in a clockwise direction. That is, the apical thread profile 46 forms a lead screw feature that simultaneously cuts into the inside walls of the hole 20 as it and forges a downward path. The apical thread profile 46 has an apical pitch and an apical lead as these terms are generally understood in the context of screw threads. That is, lead is the longitudinal distance advanced with one complete rotation (360°) of the anchor 38. Pitch is the distance from the crest of one thread to the next. If the apical thread profile 46 is designed as a single-start thread form, the apical lead and the apical pitch will be the same. Such is the case in the illustrated examples which depict the apical thread profile 46 as a single-start configuration. However, the apical thread profile 46 could alternatively be formed as a two-start (double-wound) thread pattern, meaning that there are two non-intersecting ridges of thread profile 46 wrapped around the anchor body.

The crests, i.e., outermost helical ridges, of the apical thread profile 46 very slightly taper in diameter. Compare against parallel construction lines A in FIG. 13. The root or core of the anchor 38, however, is much more aggressively tapered as can be observed by the superimposed construction lines B. The tapered shape of the root or core of the anchor 38 has the effect of outwardly condensing the host material 22 that becomes trapped between thread windings as the anchor 38 is screwed into position. The pitch of the apical thread profile 46 remains generally constant throughout the apical end 40, however, the thickness of the thread forms may (optionally) gradually increase approaching the central region 44. Thread thickness can be observed to gradually increase in the larger diameter anchor 38 examples of FIGS. 7 and 13. However, the thread thickness is seen as generally consistent in the smaller diameter anchor 38 example of FIG. 9. The very leading tip of the apical thread profile 46 may be configured with a sharp blade-like tapping feature 48. In these examples, the tapping feature 48 takes the form of a grind intended to help the advancing threads efficiently cut into the host material 22. Other strategies may be considered to assist the apical thread form 46 to tap a negative thread form into the inside walls of the hole 20. One alternative approach is described below in connection with FIG. 17. Although not shown, the extreme apex of the apical end 40 may be somewhat domed or blunted to help prevent over-insertion upon reaching hole 20 bottom.

Figure 8:
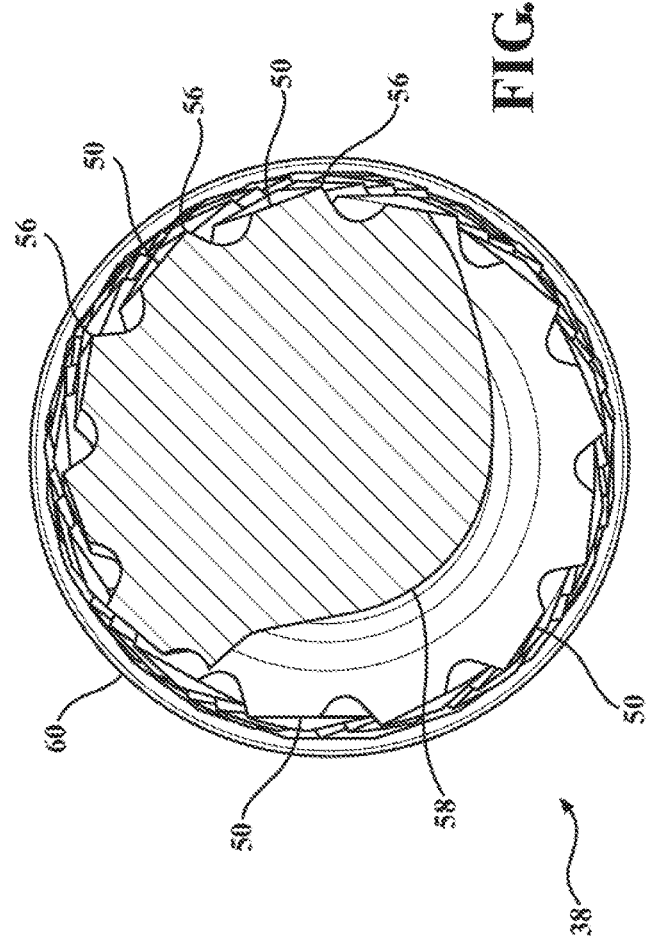
FIG. 8 is a cross-sectional view through the central region of the anchor taken generally along lines 8-8 of FIG. 7.

The central region 44 is characterized by a plurality of shallow, trough-like flutes disposed about the body. For example, the large diameter anchor 38 is shown in FIG. 8 possessing twelve flutes. The small diameter anchor 38 of FIG. 10 has only ten flutes. Naturally, larger diameters are better suited for more flutes. The flutes may be equally circumferentially arranged about the body to help maintain stability during insertion. Although the flutes could be straight axial, in the preferred embodiment the flutes having a long-lead helical twist in a left-hand direction. That is to say, the flutes preferably have a counter-twist relative to the spiraling direction of the apical thread profile 46.

Figure 14:
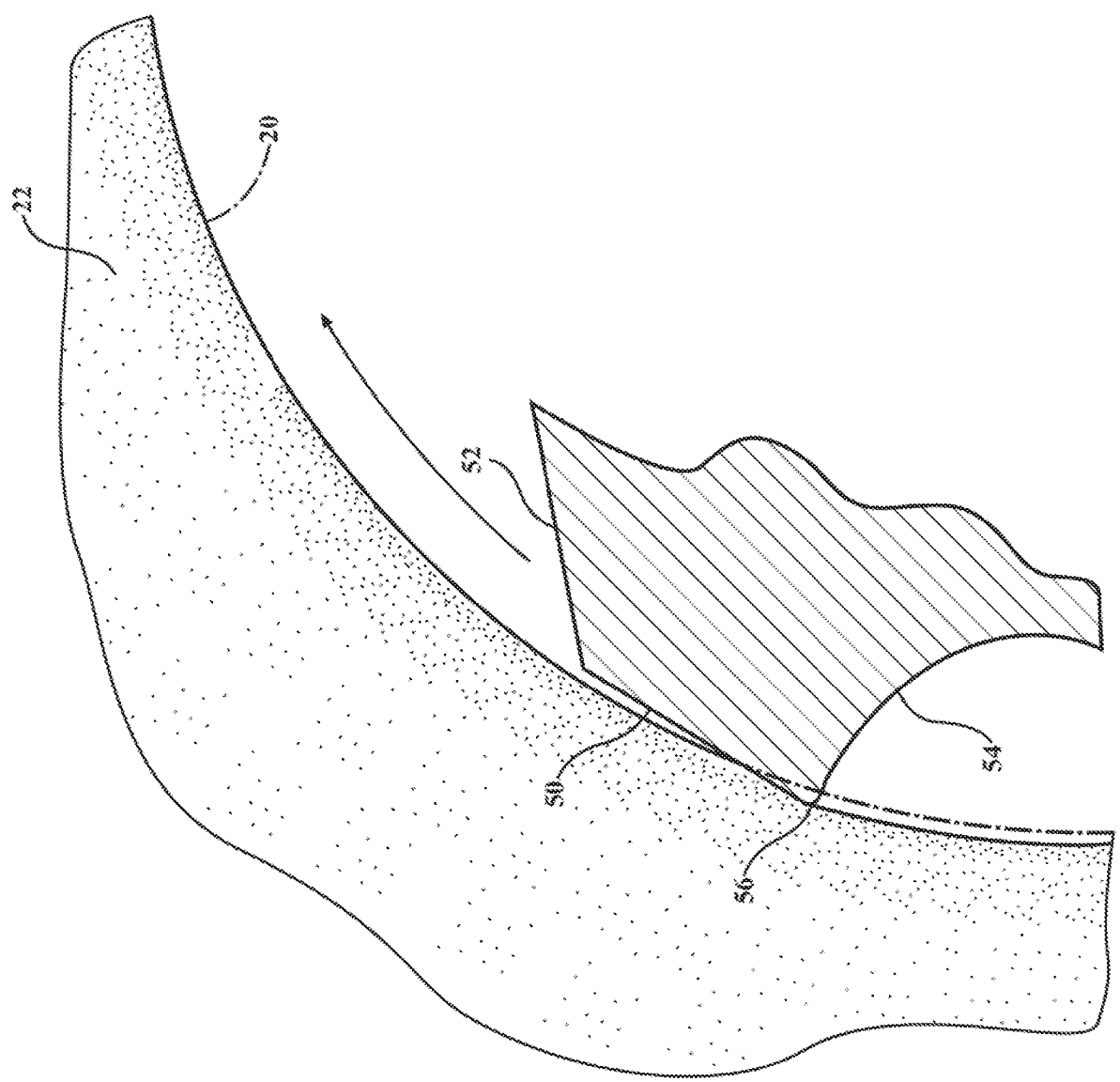
FIG. 14 is a highly-magnified view of a single condensing edge of the anchor as it wipes across the inner surface of a hole thereby outwardly displacing and inducing residual strain in the surrounding host material.
Figure 15:
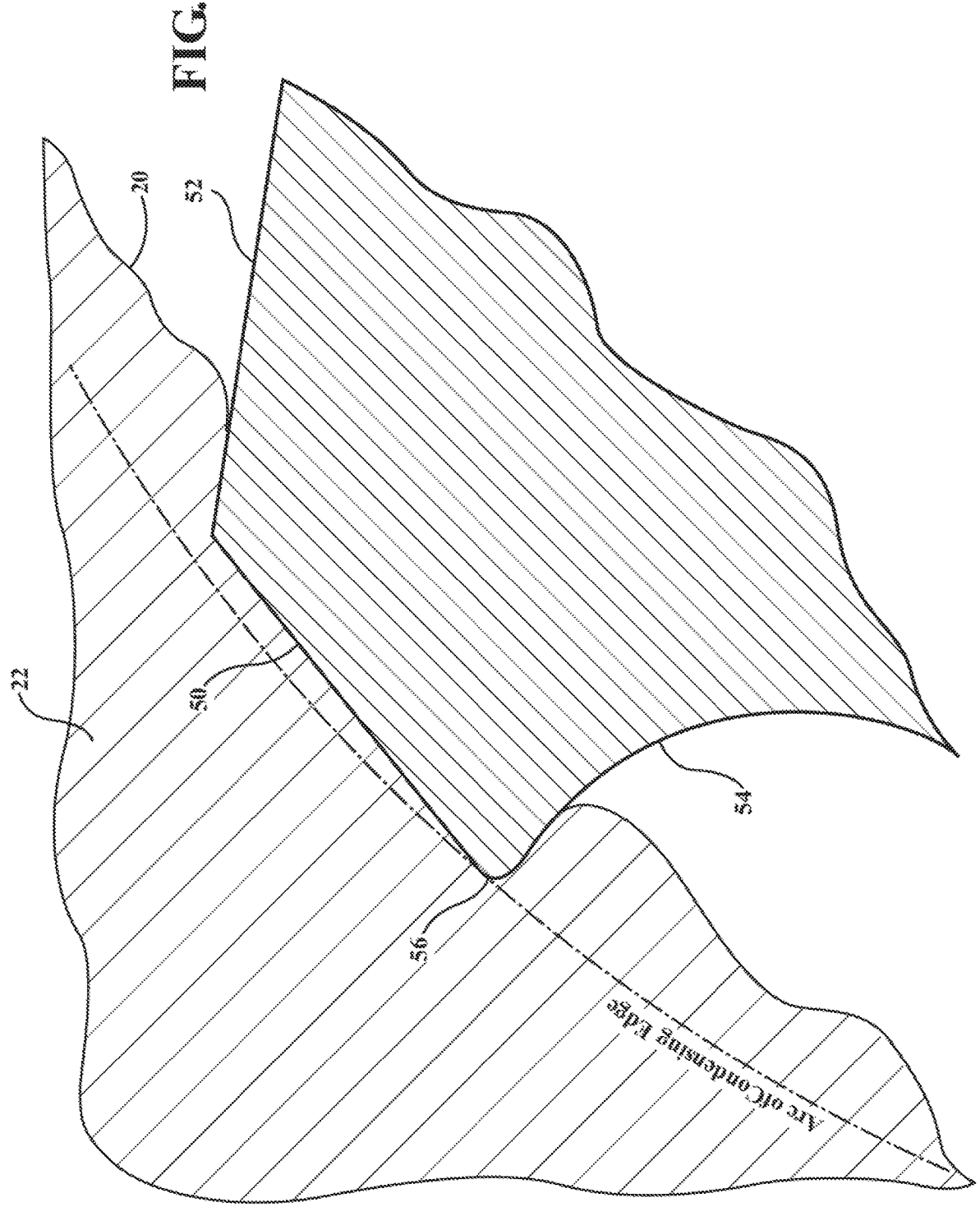
FIG. 15 is another highly-magnified view of a single condensing edge of the anchor after a period of time such that the surrounding host material exhibits a resilient response and perhaps even initial stages of in-growth, such as might occur in applications where the host material is in vivo bone.

Referring also to the highly-magnified images of FIGS. 14 and 15, a land 50 is formed between every two adjacent flutes. Each land 50 has a leading face 52 and an opposite trailing face 54. That is, as the anchor 38 is screwed into the hole 20, the leading face 52 of each land 50 precedes and its trailing flank 54 follows. Each land 50 forms a ridge-like feature having a reverse helical twist corresponding to the reverse helical twist of the interposed flutes. At the intersection of each land 50 and its trailing face 54 is a condensing edge 56. The condensing edge 56 may be substantially margin-less, meaning that the entire face of each land 50 falls away ahead of the condensing edge 56 to provide complete clearance except for the condensing edge during rotation. The primary taper clearance angle, i.e., the angle between a tangent of the condensing edge 56 and each land 50, may be anywhere between about 1° and 30° depending upon the application. Thus, the land 50 tilts into the rotational direction and serves as a ramp or wedge in front of the condensing edge 56 so that host material 22 is not cut from the inner wall of the hole 20. The condensing edges 56, therefore, are fixed (relative to the body of the anchor 38) in a non-cutting direction, meaning that the condensing edges 56 drag or wipe along the inside wall of the hole 20 with considerable negative rake rather than slicing into the inside walls like a reamer.

The condensing edges 56 are shown extending generally the full length of the central region 44, i.e., between the apical thread profile 46 and start of the coronal end 42. Like the intervening flutes, the condensing edges 56 share a left-hand helical twist, although straight axial configurations are also possible. Long leads, on the order of 1-to-3 times the overall length of the anchor 38 body, are contemplated for the lay of the condensing edges 56. The radial measure of each condensing edge 56, i.e., the distance from a central axis of the anchor 38 to the arc of the condensing edge 56 (FIG. 15), is a function of the gentle taper established by the apical thread profile 46. That is, by comparison with the parallel construction lines in FIG. 13, it can be observed that the condensing edges 56 continue the slight taper of the crests of the apical thread profile 46.

Each condensing edge 56 is interrupted by a helical groove 58. Preferably, both the shallow array of flutes and lands 50 encircling the central region 44 are interrupted by a relatively deep helical groove 58. That is, the base of the trench-like helical groove 58 is, preferably, at least as deep as the flutes so as to interrupt the full feature of the lands 50 and the flutes at each intersection along the full length of the central region 44. More preferably still, the helical groove 58 lies below the base of the flutes, having a profile between about one and four times (1×-4×) deeper than the depth of the flutes. The relative depth relationship between flutes and helical groove 58 can be kept constant along the length of the central region 44 or made variable. In the examples shown, the helical groove 58 is about three times (3×) deeper than the flutes adjacent the apical end 40, and about twice (2×) deeper than the flutes adjacent the coronal end 42. This change in depth is because the diameter at the base of the helical groove 58 is tapered generally along the same root construction lines B as the apical end 40. That is, in this embodiment the depth of the helical groove 58 throughout the central region 44, and the depth of the root of apical thread profile 46, share a common conical taper resulting in a progressively decreasing core diameter leading away from the apical end 40. Construction lines B-B bear this out. As stated previously the conical geometry of the helical grove 58 and apical thread root is designed to support superior primary stability and loading protocols.

The helical groove 58 smoothly connects with the helical root pattern established between the apical thread profile 46 in the apical end 40. That is to say, tracing the helical root pattern upwardly from the apical end 40 will lead directly and almost imperceptibly into the helical groove 58. The illustrated examples show the apical thread profile 46 as a single-start design, and in this case the helical groove 58 is likewise a single winding. Alternatively, if the apical thread profile 46 were of the double-start type then, possibly, two intertwined helical grooves would wind along the central region 44.

In the illustrated examples, the axial width of the helical groove 58 remains generally consistent along the length of the central region 44, however the pitch of the helical groove 58 changes. Preferably, but not necessarily, the winding pattern of the helical groove 58 stretches or grows as it winds toward the coronal end 42. Therefore, unlike the helical root pattern of the apical end 40 which has a pitch that remains generally constant (some minor change is possible), the pitch of the helical groove 58 progressively increases. At the juncture of the apical end 40 and central region 44, the pitch of the helical groove 58 is substantially equal to the pitch of the helical root pattern of the apical thread profile 46, which accounts for a smooth transition. This gives the appearance that the helical groove 58 is a continuous extension of helical root pattern of the apical thread profile 46. However, at the juncture of the central region 44 with the coronal end 42, the pitch of the helical groove 58 is approximately twice (2×) the pitch of the helical root pattern of the apical thread profile 46. This change in pitch is uniformly progressive, i.e., the pitch increases gracefully from ~1× to ~2× of the relatively constant apical thread profile 46 pitch. The tapered shape of the root or core of the anchor 38 (construction lines B-B in FIG. 13), in combination with the progressively changing pitch of the helical groove 58, has the effect of progressively squeezing and manipulating that affected host material 22 as the anchor 38 is screwed into place in the hole 20. The squeezing effect is not too unlike that produced by some screws in the plastic injection molding arts or the compressor section of a jet engine.

Figure 7:
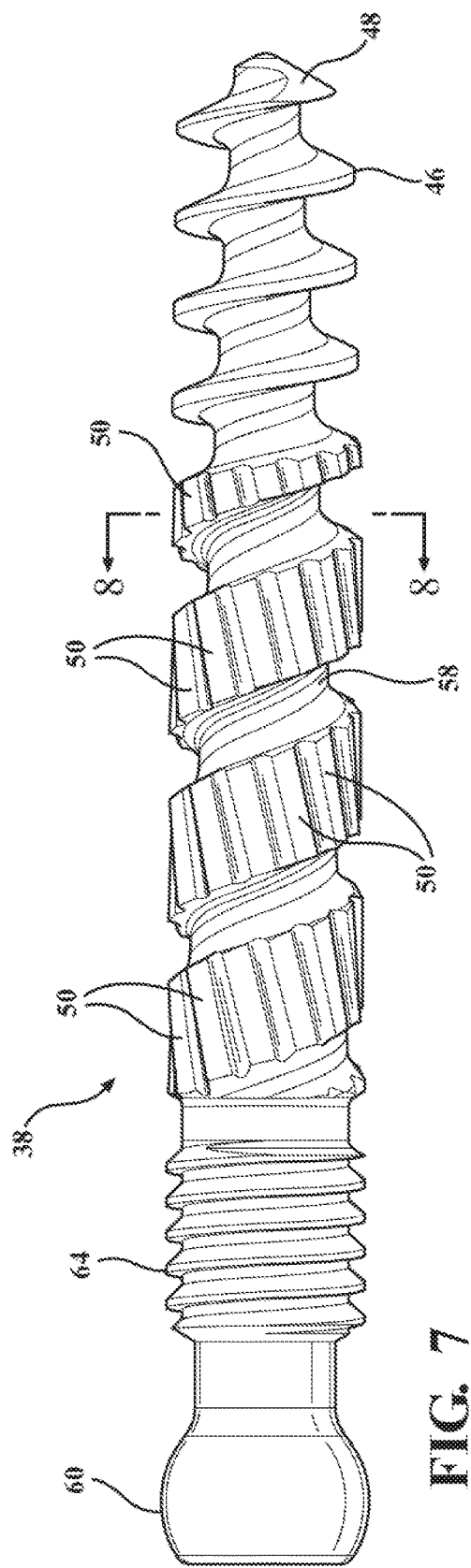
FIG. 7 is a side elevation of a large diameter anchor according to one embodiment of the present invention.
Figure 9:
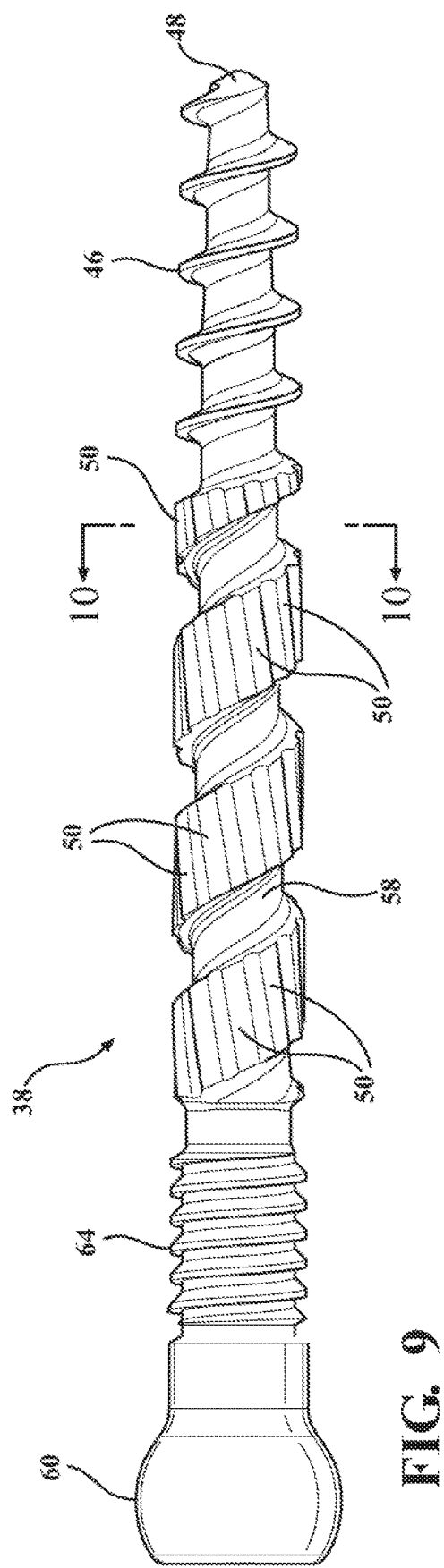
FIG. 9 is a side elevation as in FIG. 7 but showing an anchor of slightly smaller size for comparison.
Figure 10:
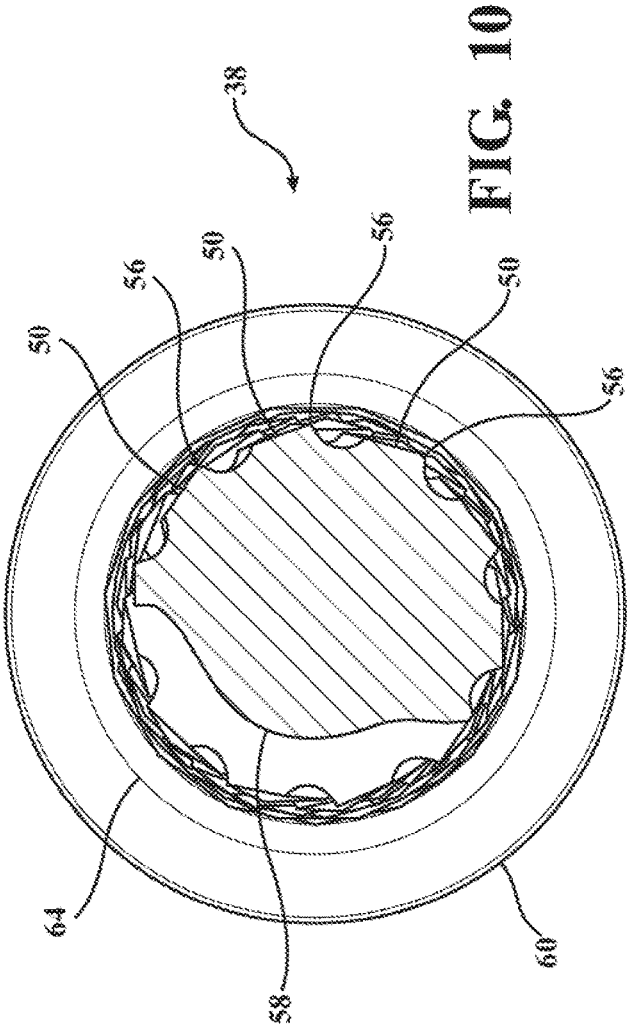
FIG. 10 is a cross-sectional view through the central region of the anchor taken generally along lines 10-10 of FIG. 9.

Along the body of the anchor 38, the propagation of the helical groove 58 helically bisects each condensing edge 56 and each flute at least once. The actual number of intersection points for the helical groove 58 with each flute/condensing edge 58 is dictated by the pitch of the helical groove 58, the left-hand twist of the flutes/condensing edges 58, and the length of the central region 44. In the example of FIGS. 7 and 9, the helical groove 58 makes about four-and-a-half (4½) turns, and bisects each flute/condensing edge 56 three or four times. Because the helical groove 58 has about the same width and depth as the helical root pattern of the apical thread profile 46, the condensing edges 56 within the central region 44 take on the appearance of a widening thread form, whose crestal ridge carries the condensing edges 56. In this manner, the combined apical thread profile 46 and helically interrupted condensing edges 56 create the appearance of a unified right-hand twist thread pattern that extends, generally uninterrupted but continuously changing in size, from the apical end 40 until run-out at the juncture with a transitional neck feature of the coronal end 42. Some of the benefits achieved by this unique configuration will be described presently.

Figure 16:
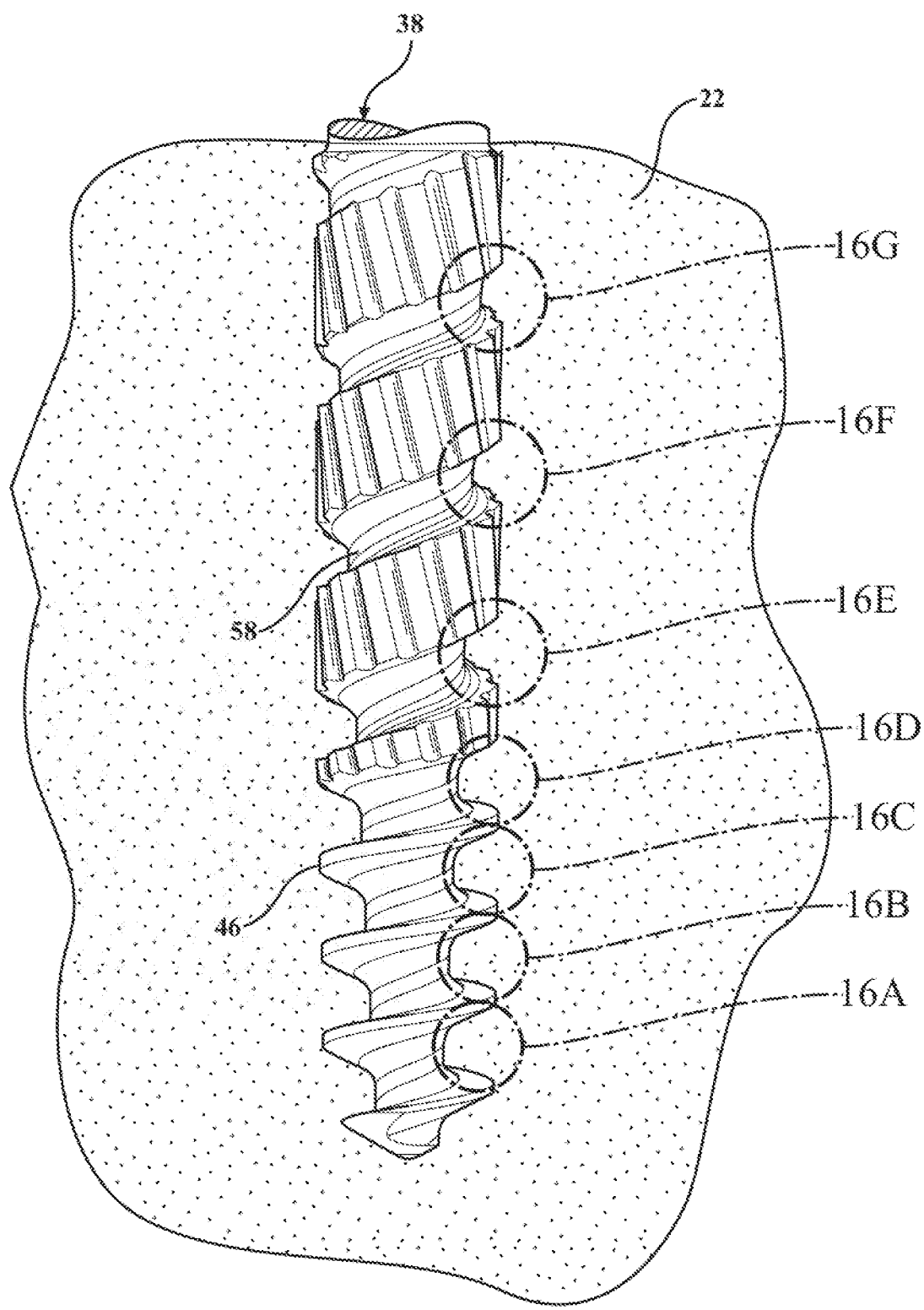
FIG. 16 is a cross-sectional view showing the embedded portion of an anchor within a hole in a host material.

In FIG. 16, an anchor 38 is shown fully seated in a host material 22. Cross-sections of impressions left by the helical root pattern are sampled at locations 16A, 16B, 16C, 16D, 16E, 16F and 16G. Notice that the axial spacing between locations 16A, 16B, 16C and 16D are relatively equal, whereas the axial spacing between locations 16D, 16E, 16F and 16G grows progressively larger. This illustrates the changing pitch of the helical groove 58 compared with the relatively constant pitch of the apical thread profile 46. FIGS. 16A-G offer a highly-simplified view of each of these locations, respectively. Each image represents host material 22 that becomes trapped and manipulated in the spiral valley upon placement of the anchor 38. The above-mentioned squeezing effect can be more readily appreciated as the anchor 38 penetrates more deeply into host material 22. In addition to squeezing, the trapped host material 22 surrounding the central region 44 of the anchor 38 is also displaced axially due to the changing pitch of the helical groove 58. This squeezing coupled with the displacement densifies the host material 22 in contact to the anchor 38, resulting in increased primary stability due to physical interlocking (higher degrees of contact) between the host material 22 and the anchor 38. In instances where the host material 22 is bone, this progressive squeezing and displacement promotes rapid new bone growth formation due to osteoblasts nucleating on the bone in close proximity with the anchor 38. Histomorphological data has demonstrated that autologous bone chips act as nucleating surfaces promoting new bone formation around an anchor, thus providing superior stability and greater bone-to-implant contact. Furthermore, the helical groove 58 and flutes and other crevices will act as chambers that will host material chips as compaction auto graft, which will promote and enhance healing in bone applications.

FIG. 14 represents a highly-magnified region of host material 22 that is acted upon by a condensing edge 56 as the anchor 38 is screwed into place. The condensing edge 56 is here seen applying a circumferentially sweeping compressive strain to the interior surface of the hole 20. The condensing edge 56 wipes and rubs against the inside wall of the hole 20 causing a concurrent enlargement of the hole 20 as well as a densification of the molecules composing the host material 22. As the anchor 38 draws itself deeper into the hole 20, the concurrent enlargement and densification of the host material 22 caused by the concerted efforts of all the condensing edges 56 produces progressively greater effects due to the slight taper of the anchor 38 and also the changing pitch of the helical groove 58. When the condensing edges 56 are formed with a left-hand helical twist as shown in FIGS. 7-13, a slight opposing axial reaction force will be generated by the condensing edges 56 dragging across the bone surface. The combination of reaction force components (normal, tangential and axial) cooperate to stress the bone material beyond its yield strength, allowing the condensing edges 56 to plow through the surface and progressively enlarge the hole 20 while concurrently accumulating stresses in the host material 22.

When the anchor 38 reaches full depth in the hole 20, accumulated stresses in the host material 22 almost immediately begin to fill into the flutes and around the condensing edges 56, as shown in FIG. 15. This rapid elastic response of the surrounding host material 22 quickly self-locks the anchor 38 in position so that it cannot be easily unscrewed, thereby providing the anchor 38 with high stability. Once all residual strain in the host material 22 has been dissipated and a state of equilibrium reached, the anchor 38 will be locked in place with maximum fixation strength. Depending on the composition characteristics of the host material 22, equilibrium may or may not result in all of the flutes and grooves and roots being completely filled.

In cases were the host material 22 is bone, however, natural regeneration and in-growth will, over time, completely fill in the voids. Soon after placement, the bone will swell and begin to grow into crevices all around the anchor 38. Bone swelling around the central region 44 more tightly self-locks the anchor 38 within the hole 20. At least some load-carrying capacity of the anchor 38 may be possible at an early stage. Over time (e.g., approximately 2-4 weeks in normal healthy bone), nearly complete bone in-growth into the crevices of the anchor 38 will occur. The anchor 38 is fully mechanically locked in the bone when healing is effectively complete.

The coronal end 42 comprises a platform 60 which defines a distal-most feature of the anchor 38. In use, the platform 60 remains exposed once the anchor 38 is fully seated in the hole 20. In some cases, such as dental implants and wall anchors for example, the platform 60 will include an internal connect that extends down into the body of the anchor 38. An internal connect is a standard, cavity-like feature found in many prior art anchor designs for applications adapted to receive the threaded post of an abutment member. Alternatively, the platform 60 could be relatively flat, like a washer-head, to distribute force over the surface of the host material 22. In the illustrated examples, which are configured for use as pedicle screws, the platform 60 has a ball-like external connect feature that mates with suitable fastener elements typically used in spinal stabilization situations like those illustrated in FIGS. 1 and 2. Naturally, the shape/design of the platform 60, be it internal or external or otherwise, can be adapted to suit the needs of the intended application, whatever that may be.

As somewhat visible in FIGS. 11 and 12, the ends of the platform 60 may include a tool-receiving socket 62. These examples show the socket 62 in the form of a star-point or polydrive type receptacle for a complimentary-shaped driver head. Of course, the form of the tool-receiving socket 62 will be matched to the application and the standards of the relevant industry/field of use.

The coronal end 42 may, optionally, be formed with a corking element 64. The corking element 64 is designed to improve host-to-anchor contact at the point of entry, and to help reduce, if not eliminate, instances of volcano-like mushrooming in the host material 22 surrounding the hole 20. The corking element 64 thus enables the installed coronal end 42 to sit neatly at or near the surface of the host material 22, thus yielding a better installation. The corking element 64 is mentioned as optional in that one may envision an anchor 38 in which no such corking feature is incorporated into the design but which enjoys other attributes and advantages of this invention. The corking element 64 can be formed in a variety of ways to achieve similar—although perhaps somewhat varied—results. In the illustrated examples, the corking element 64 is comprised of a coronal thread profile having a right-hand twist. Here, the coronal thread profile is a one-start thread pattern having a pitch that is noticeably smaller than the apical thread pitch. In particular, the pitch of the coronal thread profile is about 40% shorter than the pitch of the apical thread profile 46. An annular neck section forms a short, smooth transition between the central region 44 and coronal thread profile. The diameter of this neck section may be approximately equal to the adjoining depth of the helical groove 58 thereby facilitating a smooth flow of entrapped host material particles from the helical groove 58 into the neck section. Please refer again to the construction lines B-B in FIG. 13, which lead to termination points at the annular neck section. In this manner, the neck section serves as a useful pre-staging area for entrapped host material particles before the host material particles encounter the coronal thread profile.

The coronal thread profile may be configured with a buttress shape. In machinery, the buttress thread form is designed to handle extremely high axial thrust in one direction. The load-bearing thread face (in pull-out direction) is perpendicular to the longitudinal axis or at a slight slant (usually no greater than 7°). The other face is slanted at about 45°. When the anchor 38 is screwed into the hole 20 to a sufficient depth, the coronal thread profile engages the inner wall of the hole 20 and begins displacing host material 22 in a downward wiping direction. It should be noted that because the coronal pitch in this example is smaller than the apical pitch, the coronal thread profile will be pulled by the apical thread profile 46 into the osteotomy more quickly than they would otherwise tend to advance with clock-wise rotation. This action causes the helical crest of the coronal thread profile to pull or scrape the host material 22 down into the hole 20, including any host material 22 that may have already begun to mushroom up around the edges of the hole 20, resulting in a smoother, less disrupted surface around the hole 20. Of course, the coronal thread pattern may take many different shapes and forms.

The corking element 64, if used, can take many different configurations. Right-hand twist threads are only one possibility. Other possibilities include, but are not limited to, left-hand twist threads which would have an aggressive downward wiping effect, annular ribs, and the like.

In use, typically, a hole 20 having a diameter approximately as large as the root diameter at the apical end 40 is prepared in advance to receive the anchor 38. In some self-tapping applications, it may be acceptable to screw the anchor 38 directly into the host material 22 without a prepared hole 20. Preferably, but not necessarily, preparation of the hole 20 is accomplished using the aforementioned densifying/auto-grafting technique of FIGS. 3-6. When the anchor 38 is initially screwed into the hole 20, its apical thread profile 46 immediately slices into the inner surface of the host material 22 and propagates a downwardly spiraling path drawing the remaining body of the anchor 38 toward full seated depth. When the condensing edges 56 enter the hole 20, they begin applying circumferentially sweeping compressive strain to the interior surface of the hole 20 with a condensing action. The deeper into the hole 20 the anchor 38 descends, the greater the degree to which the condensing edges 56 wipe and rub against the host material 22. This is illustrated in somewhat exaggerated fashion in FIG. 14. However, because the host material 22 is likely to have elastic properties to some degree, there will be some "spring back" after each condensing edge 56 passes by. In this manner, the plurality of condensing edges 56 wipe the inside walls of the hole 20, one after another, as the anchor 38 is pulled down thus helping to create residual strain in the host material 22.

As the condensing edges 56 drag across the host material 22, the forces on each condensing edge 56 can be decomposed into two component forces: one normal to the surface of the host material 22, pressing it outwardly, and the other tangential, dragging it along the inner surface of the hole 20. It may be noted as well that due to the left-hand helical twist, the condensing edges 56 will also generate a slight opposing axial reaction force when concurrently forcibly advanced into the hole 20. This opposing axial reaction force works against the axial advancing direction of the anchor 38 insertion by applying force in a direction that urges the anchor 38 out of the hole 20, but is too weak to overcome the traction of the apical thread profile 46. As the tangential component is increased through clockwise rotation, the condensing edges 56 slide along the interior surfaces of the hole 20. At the same time, the normal (i.e., radial) forces along the condensing edges 56 will deform the host material 22, especially if it is relatively soft like trabecular bone for example. The residual strain thus introduced into the surface of the host material 22 will exceed its yield strength, allowing the condensing edges 56 to plow through the surface like a burnishing operation. The plowing action of the condensing edges 56, as depicted in FIG. 14, thus affects the mechanical properties of the entire interior surface of the hole 20.

Stresses applied through the condensing edges 56 continue to accumulate all around the hole 20. When the anchor 38 reaches full depth and stops rotating, the built-up stresses in the host material 22 are released from captivity so-to-speak, thus provoking the previously described spring-back action to lock the condensing edges 56 into position as graphically depicted in FIG. 15. This almost immediate elastic response of the host material 22 to the loading of stresses from the screw-in operation, and possibly also having accumulated during earlier hole preparation, provides a favorable high initial anchor 38 stability. Furthermore, the portions of host material 22 that elastically expand in the flutes effectively self-locks the anchor 38 in position so that it cannot easily be removed by unscrewing. Another benefit of this anchor 38 with condensing edges 56 is its ability to strengthen the fabric of certain types of host materials 22. For examples, when bone or wood or foam (to name a few) is subjected to stress in the region between its yield point and its ultimate tensile strength, the material experiences strain hardening. Strain hardening, also known as work hardening or cold working, is the strengthening of a ductile material by plastic deformation. This strengthening occurs because of dislocation movements and dislocation generation within the crystal structure of the material. And yet another benefit of this anchor 38 is found specifically in bone applications where the condensing edges 56 and other special attributes have the ability to activate natural bone re-generation.

The method of use may therefore be described as screwing an anchor 30 progressively deeper into a prepared hole 20 while concurrently applying a circumferentially sweeping compressive strain to the interior surface of the hole 20 with an array of condensing edges 56. As the condensing edges 56 drag across the inner surface of the hole 20, stresses accumulate in the side walls. When the anchor 38 reaches full depth and stops rotating, the built-up stresses are no longer restrained so that the host material 22 fills in around the condensing edges 56. A rapid elastic response provides a favorable high initial anchor 38 stability, self-locks the anchor 38 in position so that it cannot be easily removed by unscrewing, and strengthens the surrounding walls of the hole 20. In bone applications, natural bone re-generation is stimulated for successful long-term anchor 38 stability.

FIG. 17 shows an alternative embodiment of the present invention. In this example, features of the anchor 138 corresponding to those described in the preceding examples are identified with like reference numerals but with a 1-prefix (i.e., offset by 100). This example is also configured for orthopedic applications like the aforementioned pedicle screw context of FIGS. 1 and 2. The apical 140 and coronal 142 ends are relatively short in comparison to the central region 144. It may be said that the apical end 140 and the coronal end 142 are each about ⅕ the overall length of the anchor 138. And the central region 144 is about ⅗ the overall length of the anchor 138.

The apical thread profile 146 is designed to make the anchor 138 self-tapping without a pilot hole or perhaps merely a relatively small pilot hole. Self-tapping indicates the ability for the anchor 138 to advance when turned, while creating its own thread. This self-tapping ability is facilitated by grinding at least one pocket 148 in the continuity of the apical thread profile 146. The pocket(s) 148 help cut complementary threads in the surrounding walls of the hole as the anchor 138 is screwed in the clockwise direction. The pocket 148 will collect host chips during insertion.

In the central region 144, there is not a helical groove that connects to the root of the apical thread profile 146 as in the earlier examples. However, the flutes and lands 50 are not continuous. An intermediate thread form 166 interrupts the condensing edges 156 in the central region 144. The intermediate thread form 166 may or may not have a pitch that is generally equal to the pitch of the apical thread profile 146. When inserting the anchor 138 into a hole, the intermediate thread form 166 serves as a booster for the tractive efforts of the apical thread profile 146 to help avoid stripping out the apical thread profile 146 in softer host materials.

In the coronal end 142, coronal thread profiles form a corking element 164. An annular neck section serves as a transition to the coronal thread profiles from the central region 144. These coronal thread profiles share approximately the same pitch as that of the apical thread profile 146 and the intermediate thread form 166. With generally matched pitches, the three sets of threads (one in each section 140, 142, 144) cooperate during insertion.

In orthopedic applications, an anchor 38, 138 according to this invention is capable of reaching sufficient anchor stability at the time of initial placement. Furthermore, because of its unique ability to promote bone regeneration, long-term anchor stability is both enhanced and accelerated. The unique condensing attributes of this invention are compatible with many of the prior art variations in thread shape, surface texture and/or special coatings.

Furthermore, the concepts of this invention may be adapted to form relatively short anchors used as dental implants along the lines described in the Applicant's patent application WO 2014/093487 published Jun. 19, 2014. The entire disclosure of WO 2014/093487 is hereby incorporated by reference as may be permitted by applicable laws in each jurisdiction.

To reiterate, the principles of this invention are not limited to bone as the host material 22. Indeed, the condensing anchor 38, 138 of this invention may be configured to establish fixation in almost any type of material, both cellular and non-cellular, provided it suitable elastic response characteristics so that when the anchor 38, 138 reaches full depth, accumulated strain in the surrounding material will fill in around the condensing edges 56, 156 and other crevices more-or-less like that illustrated in FIG. 15. This elastic response of the surrounding material self-locks the anchor 38, 138 in position so that it cannot be easily unscrewed thereby providing the anchor 38, 138 with high initial stability. When the host material 22 has living characteristic, healing-induced in-growth will produce even stronger purchase. For example, when the anchor 38, 138 is screwed into a live tree, the living cells of the wood will grow into the crevices of the anchor 38. Likewise, when the anchor 38, 138 is screwed into in vivo bone, the in-growth described above will provide a substantially enhanced fixation. Non-organic applications are not to be minimized. For example, the anchor 38, 138 may be used in metal foam of the type used extensively in aerospace, heat shielding and other critical applications. Additional contemplated application of the anchor 38, 138 include civil engineering scenarios in earthen holes of soft, loose soils and muck. Indeed, many other applications may also present due to the unique condensing qualities of the anchor 38, 138.

Throughout this description, reference is made to right-hand and left-hand threads. Right-hand threads advance under clockwise rotation and conversely left-hand threads advance under counter-clockwise rotation. Right-hand threads are by overwhelming proportion most common and therefore such usage has been carried throughout this description. It should be understood, however, that reversal of all thread patterns from right-handed to left-handed (and vise-versa) is possible and will result in substantially identical performance characteristics with counter-clockwise rotation upon insertion. Left-handed twist for the apical thread profile 46 is thus considered a mere structural equivalent to the disclosed and claimed embodiments herein. Said another way, if one of the clockwise or counter-clockwise directions are deemed a "first" rotatory direction and the other of the clockwise and counter-clockwise directions are deemed a "second" rotary direction, then it would be accurate to say that if the apical thread profile 46, 146 is formed in the first rotary direction, then the helical twist of the condensing edges 56, 156, are preferably in the second rotary direction or straight (i.e., infinite lead) and angled in a non-cutting direction so as not to cut material from the inner wall of the hole 20.

The foregoing invention has been described in accordance with the relevant legal standards, thus the description is exemplary rather than limiting in nature. Use of any terms that may be customarily associated with a particular field must not be narrowly construed so as to limit the supposed application of the invention to that particular field of use. Variations and modifications to the disclosed embodiment may become apparent to those skilled in the art and fall within the scope of the invention.

What is claimed is:

1. An anchor of the type screwed into a host material, said anchor comprising:
   a body having an apical end and a coronal end, a central region of said body extending between said apical end and said coronal end,
   said apical end having an apical thread profile for advancing said body progressively deeper into the host material as said body is forcibly turned in a first rotary direction,
   said central region including an array of longitudinally extending flutes with intervening lands, each said flute having a depth, each said land forming a condensing edge configured to apply a circumferentially sweeping compressive strain to the interior surface of the host material with a densifying action while said anchor is being screwed into position, and
   at least one helical groove spiraling along said central region and intersecting each of said condensing edges at least once, and
   wherein said apical thread profile forms at least one helical root pattern, said helical groove directly adjoining said helical root pattern as a continuous extension thereof.

2. The anchor of claim 1 wherein said helical groove has a depth equal to or greater than the depth of said flutes.

3. The anchor of claim 2 wherein the depth of said helical groove is between about one and four times the depths of said flutes.

4. The anchor of claim 1 wherein said apical thread profile has a generally constant pitch, said helical groove has a variable pitch.

5. The anchor of claim 4 wherein said variable pitch of said helical groove is generally equal to said pitch of said apical thread profile adjacent said apical end, and said variable pitch of said helical groove is greater than said pitch of said apical thread profile adjacent said coronal end.

6. The anchor of claim 1 wherein said anchor has a continuously tapered root core diameter over said central region and said apical end.

7. The anchor of claim 1 wherein said apical thread profile is a single-start.

8. The anchor of claim 1 wherein said apical thread profile has a right-hand twist and each said condensing edge has a left-hand helical twist, said flutes having a left-hand helical twist corresponding to said left-hand twist of said condensing edges.

9. A pedicle screw comprising:
   a body having an apical end and a coronal end, a central region of said body extending between said apical end and said coronal end,
   said apical end having an apical thread profile for advancing said body progressively deeper into an osteotomy as said body is forcibly turned in a first rotary direction,
   said central region including an array of longitudinally extending flutes with intervening lands, each said flute having a depth, each said land forming a condensing edge configured to apply a circumferentially sweeping compressive strain to the interior surface of the osteotomy with a densifying action while said pedicle screw is being screwed into position, at least one helical groove spiraling along said central region and intersecting each of said condensing edges at least once, and wherein said apical thread profile forms at least one helical root pattern, said helical groove directly adjoining said helical root pattern as a continuous extension thereof.

10. The pedicle screw of claim 9 wherein said helical groove has a depth equal to or greater than the depth of said flutes.

11. The pedicle screw of claim 9 wherein said apical thread profile has a generally constant pitch, said helical groove has a variable pitch, said variable pitch of said helical groove is generally equal to said pitch of said apical thread profile adjacent said apical end, and said variable pitch of said helical groove is greater than said pitch of said apical thread profile adjacent said coronal end.

12. An anchor of the type screwed into a prepared hole in a host material, said anchor comprising:

a body having an apical end and a coronal end, a central region of said body extending between said apical end and said coronal end, said apical end having an apical thread profile for advancing said body progressively deeper into the hole as said body is forcibly turned in a right-hand rotary direction, said apical thread profile forming at least one helical root pattern, said apical thread profile having a generally constant pitch, said central region including an array of longitudinally extending flutes with intervening lands, each said flute having a depth, each said land forming a condensing edge configured to apply a circumferentially sweeping compressive strain to the interior surface of the host material with a densifying action while said anchor is being screwed into the prepared hole, each said condensing edge having a left-hand helical twist, said flutes having a left-hand helical twist corresponding to said left-hand twist of said condensing edges, and at least one helical groove spiraling along said central region and intersecting each of said condensing edges at least once, said helical groove having a depth between about one and four times the depths of said flutes, said helical groove directly adjoining said helical root pattern as a continuous extension thereof, said helical groove having a variable pitch generally equal to said pitch of said apical thread profile adjacent said apical end, said variable pitch of said helical groove is greater than said pitch of said apical thread profile adjacent said coronal end.

* * * * *